(12) United States Patent
Ota et al.

(10) Patent No.: US 7,029,860 B2
(45) Date of Patent: Apr. 18, 2006

(54) AMYLOID-β PROTEIN AGGREGATION-REGULATING FACTORS

(75) Inventors: Toshio Ota, Machida (JP); Takao Isogai, Inashiki-gun (JP); Tetsuo Nishikawa, Itabashi-ku (JP); Yuri Hio, Kisarazu (JP); Mayako Yamazaki, Toride (JP); Susumu Satoh, Tsukuba-gun (JP); Hiroyuki Arakawa, Tsukuba (JP); Masahiko Morita, Ushiku (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 35 days.

(21) Appl. No.: 11/013,400

(22) Filed: Dec. 17, 2004

(65) Prior Publication Data

US 2005/0214813 A1   Sep. 29, 2005

Related U.S. Application Data

(62) Division of application No. 10/030,269, filed as application No. PCT/JP00/04515 on Jul. 6, 2000.

(60) Provisional application No. 60/159,586, filed on Oct. 18, 1999.

(30) Foreign Application Priority Data

Jul. 8, 1999   (JP) ................................ 11-194179

(51) Int. Cl.
  *G01N 33/50*   (2006.01)
  *A61K 38/17*   (2006.01)
  *C07K 14/435*  (2006.01)

(52) U.S. Cl. .................. 435/7.1; 514/12; 530/350; 530/387.1

(58) Field of Classification Search .................... None
See application file for complete search history.

(56) References Cited

FOREIGN PATENT DOCUMENTS

| EP | 979870    |      | 2/2000 |
|----|-----------|------|--------|
| EP | 1067182   | A2   | 1/2001 |
| EP | 1067182   | A3   | 1/2001 |
| EP | 1067182   | A8   | 1/2001 |
| WO | 98/21328  |      | 5/1998 |
| WO | 99/55865  |      | 11/1999|

OTHER PUBLICATIONS

J. Rankin, et al., "Partial cloning and assignment[1] of WNTA to human chromosome bank 2q35 by in situ hybridization", Cytogenet Cell Genet. vol. 84(1-2), 1999, p. 50-52.
GENBANK Accession No. AF079522, Jul. 1, 1999.
B. H. Anderton, "Alzheimer's disease: Clues from flies and worms", Current Biology, vol. 9(3), 1999, p. R106-R109.
A. Caricasole, et al., "The Wnt pathway, cell-cycle activation and β-amyloid: novel therapeutic strategies in Alzheimer's disease?", Trends in Pharmacological Sciences, vol. 24(5), 2003, p. 233-238.
B.J. Gavin et al., "Expression of multiple novel Wnt-1/Int-1-related genes during fetal and adult mouse developments" Genes & Development, vol. 4, No. 12B, pp. 2319-2332, 1990.
J. Ghanta et al., "A strategy for designing inhibitors of beta-amyloid toxicity", Journal of Biological Chemistry, vol. 271, No. 47, pp. 29525-29528, 1996.
Y. Du et al., "alpha2-Macroglobulin attenuates beta-amyloid peptid 1-40 fibril formation and associated neurotoxicity of cultured fetal rat", Journal of Neurochemistry, vol. 70, No. 3, pp. 1182-1188, 1998.
M.M. Pallito et al., "Recognition sequence design for peptidyl modulators of beta-amyloid aggregation and toxicity", Biochemistry, vol. 38, No. 12, pp. 3570-3578, Mar. 1999.
H. Levine III, et al., "Quantification of -sheet amyloid fibril structures with thioflavin T", Methods in Enzymology, vol. 309, pp. 274-284, Oct. 1999.
Inestrosa, et al., "Acetyicholinesterase accelerates assembly of amyloid-beta-peptides into Alzheimer's fibrils: possible role of the peripheral site of the enzyme," Neuron. Apr. 1996, vol. 16, No. 4, pp. 881-891.
Drouet, et al., "Laminin 1 attenuates beta-amyloid peptide Abeta (1-40) neurotoxicity of cultured fetal rat cortical neurons." Journal of Neurochemistry. Aug. 1999, vol. 73, No. 2, pp. 742-749.

*Primary Examiner*—Robert A. Wax
(74) *Attorney, Agent, or Firm*—Oblon, Spivak, McClelland, Maier & Neustadt, P.C.

(57) ABSTRACT

The present invention provides: proteins suppressing or promoting the aggregation or deposition of amyloid-β protein; polynucleotides encoding the proteins; a method for screening a compound suppressing or promoting the aggregation or deposition of amyloid-β protein; and therapeutic agents for treating or preventing Alzheimer's diseases comprising a compound that regulates the activity of a protein suppressing or promoting the aggregation or deposition of amyloid-β protein.

18 Claims, No Drawings

SEQUENCE LISTING

<160> NUMBER OF SEQ ID NOS: 22

<210> SEQ ID NO 1
<211> LENGTH: 1499
<212> TYPE: DNA
<213> ORGANISM: Homo sapiens
<220> FEATURE:
<221> NAME/KEY: CDS
<222> LOCATION: (58)..(606)
<223> OTHER INFORMATION:

<400> SEQUENCE: 1

```
gcggctgcag cgggcttgta ggtgtccggc tttgctggcc cagcaagcct gataagc          57 atg aag ctc tta tct ttg gtg gcc gtg gtc ggg tgt ttg ctg gtg ccc         105
Met Lys Leu Leu Ser Leu Val Ala Val Val Gly Cys Leu Leu Val Pro
1               5                   10                  15 cca gct gaa gcc aac aag agt tct gaa gat atc cgg tgc aaa tgc atc         153
Pro Ala Glu Ala Asn Lys Ser Ser Glu Asp Ile Arg Cys Lys Cys Ile
                20                  25                  30 tgt cca cct tat aga aac atc agt ggg cat att tac aac cag aat gta         201
Cys Pro Pro Tyr Arg Asn Ile Ser Gly His Ile Tyr Asn Gln Asn Val
            35                  40                  45 tcc cag aag gac tgc aac tgc ctg cac gtg gtg gag ccc atg cca gtg         249
Ser Gln Lys Asp Cys Asn Cys Leu His Val Val Glu Pro Met Pro Val
        50                  55                  60 cct ggc cat gac gtg gag gcc tac tgc ctg ctg tgc gag tgc agg tac         297
Pro Gly His Asp Val Glu Ala Tyr Cys Leu Leu Cys Glu Cys Arg Tyr
65                  70                  75                  80 gag gag cgc agc acc acc acc atc aag gtc atc att gtc atc tac ctg         345
Glu Glu Arg Ser Thr Thr Thr Ile Lys Val Ile Ile Val Ile Tyr Leu
                85                  90                  95 tcc gtg gtg ggt gcc ctg ttg ctc tac atg gcc ttc ctg atg ctg gtg         393
Ser Val Val Gly Ala Leu Leu Leu Tyr Met Ala Phe Leu Met Leu Val
            100                 105                 110 gac cct ctg atc cga aag ccg gat gca tac act gag caa ctg cac aat         441
Asp Pro Leu Ile Arg Lys Pro Asp Ala Tyr Thr Glu Gln Leu His Asn
        115                 120                 125 gag gag gag aat gag gat gct cgc tct atg gca gca gct gct gca tcc         489
Glu Glu Glu Asn Glu Asp Ala Arg Ser Met Ala Ala Ala Ala Ala Ser
    130                 135                 140 ctc ggg gga ccc cga gca aac aca gtc ctg gag cgt gtg gaa ggt gcc         537
Leu Gly Gly Pro Arg Ala Asn Thr Val Leu Glu Arg Val Glu Gly Ala
145                 150                 155                 160 cag cag cgg tgg aag ctg cag gtg cag gag cag cgg aag aca gtc ttc         585
Gln Gln Arg Trp Lys Leu Gln Val Gln Glu Gln Arg Lys Thr Val Phe
                165                 170                 175 gat cgg cac aag atg ctc agc tagatgggct ggtgtggttg ggtcaaggcc            636
Asp Arg His Lys Met Leu Ser
                180 ccaacaccat ggctgccagc ttccaggctg gacaaagcag ggggctactt ctcccttccc       696 tcggttccag tcttcccttt aaaagcctgt ggcattttc ctccttctcc ctaactttag        756 aaatgttgta cttggctatt ttgattaggg aagagggatg tggtctctga tctctgttgt       816 cttcttgggt ctttgggggtt gaagggatgg ggaaggcagg ccagaaggga atggagacat     876 tcgaggcggc ctcaggagtg gatgcgatct gtctctcctg gctccactct tgccgccttc      936 cagctctgag tcttgggaat gttgttaccc ttggaagata aagctgggtc ttcaggaact      996 cagtgtctgg gaggaaagca tggcccagca ttcagcatgt gttcctttct gcagtggttc     1056
```

-continued

```
ttatcaccac ctccctccca gccccagcgc ctcagcccca gccccagctc cagccctgag      1116
gacagctctg atgggagagc tgggccccct gagcccactg ggtcttcagg gtgcactgga      1176
agctggtgtt cgctgtcccc tgtgcacttc tcgcactggg gcatggagtg cccatgcata      1236
ctctgctgcc ggtcccctca cctgcacttg aggggtctgg gcagtccctc ctctccccag      1296
tgtccacagt cactgagcca gacggtcggt tggaacatga gactcgaggc tgagcgtgga      1356
tctgaacacc acagccctg tacttgggtt gcctcttgtc cctgaacttc gttgtaccag       1416
tgcatggaga gaaaattttg tcctcttgtc ttagagttgt gtgtaaatca aggaagccat      1476
cattaaattg ttttatttct ctc                                             1499
```

<210> SEQ ID NO 2
<211> LENGTH: 183
<212> TYPE: PRT
<213> ORGANISM: Homo sapiens

<400> SEQUENCE: 2

```
Met Lys Leu Leu Ser Leu Val Ala Val Val Gly Cys Leu Leu Val Pro
1               5                   10                  15

Pro Ala Glu Ala Asn Lys Ser Ser Glu Asp Ile Arg Cys Lys Cys Ile
                20                  25                  30

Cys Pro Pro Tyr Arg Asn Ile Ser Gly His Ile Tyr Asn Gln Asn Val
            35                  40                  45

Ser Gln Lys Asp Cys Asn Cys Leu His Val Val Glu Pro Met Pro Val
        50                  55                  60

Pro Gly His Asp Val Glu Ala Tyr Cys Leu Leu Cys Glu Cys Arg Tyr
65                  70                  75                  80

Glu Glu Arg Ser Thr Thr Thr Ile Lys Val Ile Ile Val Ile Tyr Leu
                85                  90                  95

Ser Val Val Gly Ala Leu Leu Leu Tyr Met Ala Phe Leu Met Leu Val
            100                 105                 110

Asp Pro Leu Ile Arg Lys Pro Asp Ala Tyr Thr Glu Gln Leu His Asn
        115                 120                 125

Glu Glu Glu Asn Glu Asp Ala Arg Ser Met Ala Ala Ala Ala Ala Ser
    130                 135                 140

Leu Gly Gly Pro Arg Ala Asn Thr Val Leu Glu Arg Val Glu Gly Ala
145                 150                 155                 160

Gln Gln Arg Trp Lys Leu Gln Val Gln Glu Gln Arg Lys Thr Val Phe
                165                 170                 175

Asp Arg His Lys Met Leu Ser
            180
```

<210> SEQ ID NO 3
<211> LENGTH: 1828
<212> TYPE: DNA
<213> ORGANISM: Homo sapiens
<220> FEATURE:
<221> NAME/KEY: CDS
<222> LOCATION: (83)..(487)
<223> OTHER INFORMATION:

<400> SEQUENCE: 3

```
aagcgacgac ttccgccctc cttagggccg tggtcccgta gctaccggtc gcgtcgccgt       60
gggcgacgtg cccgcttcca aa atg gcg gcg gcg gcg gta tct ggt gcg ctt      112
                         Met Ala Ala Ala Ala Val Ser Gly Ala Leu
                         1               5                   10
```

-continued

| | | |
|---|---|---|
| ggc cgg gcg ggc tgg agg ctc ctg cag ctg cga tgc ctg ccc gtg gcc<br>Gly Arg Ala Gly Trp Arg Leu Leu Gln Leu Arg Cys Leu Pro Val Ala<br>                   15                              20                       25 | 160 |
| cgt tgc cga caa gcc ctg gtg ccg cgt gcc ttc cat gct tca gct gtg<br>Arg Cys Arg Gln Ala Leu Val Pro Arg Ala Phe His Ala Ser Ala Val<br>                30                              35                       40 | 208 |
| ggg cta agg tct tca gat gag cag aag cag cag cct ccc aac tca ttt<br>Gly Leu Arg Ser Ser Asp Glu Gln Lys Gln Gln Pro Pro Asn Ser Phe<br>       45                            50                            55 | 256 |
| tct cag cag cat tct gag aca cag ggc gca gaa aaa cct gat cca gag<br>Ser Gln Gln His Ser Glu Thr Gln Gly Ala Glu Lys Pro Asp Pro Glu<br>60                           65                            70 | 304 |
| tct tct cat tca ccc ccc agg tat aca gac cag ggc ggc gag gag gag<br>Ser Ser His Ser Pro Pro Arg Tyr Thr Asp Gln Gly Gly Glu Glu Glu<br>75                           80                            85                       90 | 352 |
| gag gac tat gaa agt gag gag cag ttg cag cac cgc atc ctg acg gca<br>Glu Asp Tyr Glu Ser Glu Glu Gln Leu Gln His Arg Ile Leu Thr Ala<br>                95                           100                      105 | 400 |
| gcc ctt gag ttt gtg ccc gcc cac ggg tgg aca gca gag gcg att gca<br>Ala Leu Glu Phe Val Pro Ala His Gly Trp Thr Ala Glu Ala Ile Ala<br>                110                         115                      120 | 448 |
| gaa gga gcc cag gtg tgt ata ggt gag ggt ggg gcc acc taaccaagat<br>Glu Gly Ala Gln Val Cys Ile Gly Glu Gly Gly Ala Thr<br>            125                         130                      135 | 497 |
| gagccaggat ggagtcacac caggcagagc gggggcctc atgccttctt ccagtctagc | 557 |
| tcagagcccc tcacagctgc aagattgact ggttttttc ccccaatagg gtggaactgg | 617 |
| ctttattttg tagttataaa aacatacca tggagttggt tcttgggagt tgtgttctaa | 677 |
| aggcaatcta ttaggcaaga attgtctgtg atcaaaactc ccatgtttca ttgactctaa | 737 |
| gatgccattg gttgtaagaa gcatcatttt taaatgcatc agtaaaaaag aaaacatact | 797 |
| gcccttcgaa ctatgacaaa gcacttctgt gattcacact gattttttaa aatgaaaaat | 857 |
| atatctgcat cttagaatta atgacatatg gtgtttgaaa accccaaga aggcaccact | 917 |
| ttggagacca acacatctta ttttcccaga aactctaata gcattttctg cattagtaca | 977 |
| gactgctgct ttagattagg cagcaggctc atgttcaggc catgttgtag agaatcctcc | 1037 |
| agcatagcaa gataccatcc tccaagagac tgaggggatg acagagttgc atcttccatc | 1097 |
| ccaggcttgc tgcagggcat ctacccatgg acaatgggca aggttgctgc tttactgaaa | 1157 |
| tttaactgtt atttccttgt cttctctcac tcccaagtgc acatttggta acagaagtct | 1217 |
| cattagtgaa atgtgggtgc tctgactcca ctgtaggctc attgtgaaaa ctgaacaata | 1277 |
| caaacaaata taaaaagaa tgtagaaaac acctataatc acaccaaaga tcatactatc | 1337 |
| aacatttatg cctagatctt tccaattaaa acccttata tgattcattc tttaaatgtt | 1397 |
| tattgagcaa ataatgtgcc ctaggcactg tgctagtcca agagacatga cagggtcaa | 1457 |
| agtggtcaag atggatctgc ttcctgccct tgttgagctt ccagtctagc aacattaata | 1517 |
| aaatatatac aaatgtttac ttagaagatg tggtaagtgc tatcaaggaa aggtgctgtt | 1577 |
| gggctgtata atggagggac ccgatcatta gatcaggtca cagctgcgag attgactggt | 1637 |
| ttctttccct caatagggtg gaaatggctt tattttgtgg atataaaagt aatgaaccat | 1697 |
| ggaattggtt cttgagagtt gtgttctaaa ggcaacctat tggcaagaat tgtctgtgat | 1757 |
| caaaactacc atatttcatt gactctaaga tgccattggt tgtaagaagc actattttta | 1817 |
| agtacatcag t | 1828 |

<210> SEQ ID NO 4
<211> LENGTH: 135
<212> TYPE: PRT
<213> ORGANISM: Homo sapiens

<400> SEQUENCE: 4

```
Met Ala Ala Ala Ala Val Ser Gly Ala Leu Gly Arg Ala Gly Trp Arg
1               5                   10                  15
Leu Leu Gln Leu Arg Cys Leu Pro Val Ala Arg Cys Arg Gln Ala Leu
            20                  25                  30
Val Pro Arg Ala Phe His Ala Ser Ala Val Gly Leu Arg Ser Ser Asp
        35                  40                  45
Glu Gln Lys Gln Gln Pro Pro Asn Ser Phe Ser Gln Gln His Ser Glu
    50                  55                  60
Thr Gln Gly Ala Glu Lys Pro Asp Pro Glu Ser Ser His Ser Pro Pro
65                  70                  75                  80
Arg Tyr Thr Asp Gln Gly Gly Glu Glu Glu Asp Tyr Glu Ser Glu
                85                  90                  95
Glu Gln Leu Gln His Arg Ile Leu Thr Ala Ala Leu Glu Phe Val Pro
            100                 105                 110
Ala His Gly Trp Thr Ala Glu Ala Ile Ala Glu Gly Ala Gln Val Cys
        115                 120                 125
Ile Gly Glu Gly Gly Ala Thr
    130                 135
```

<210> SEQ ID NO 5
<211> LENGTH: 1584
<212> TYPE: DNA
<213> ORGANISM: Homo sapiens
<220> FEATURE:
<221> NAME/KEY: CDS
<222> LOCATION: (100)..(1194)
<223> OTHER INFORMATION:

<400> SEQUENCE: 5

```
gcgctcgccg cgctcgcact gaagcccggg ccctcgcgcg ccgcggttcg ccccgcagcc     60
tcgccccctg cccacccggg cggccgtagg gcggtcacg atg ctg ccg ccc tta       114
                                          Met Leu Pro Pro Leu
                                          1               5 ccc tcc cgc ctc ggg ctg ctg ctg ctg ctc ctg tgc ccg gcg cac          162
Pro Ser Arg Leu Gly Leu Leu Leu Leu Leu Leu Cys Pro Ala His
                10                  15                  20 gtc ggc gga ctg tgg tgg gct gtg ggc agc ccc ttg gtt atg gac cct     210
Val Gly Gly Leu Trp Trp Ala Val Gly Ser Pro Leu Val Met Asp Pro
            25                  30                  35 acc agc atc tgc agg aag gca cgg cgg ctg gcc ggg cgg cag gcc gag     258
Thr Ser Ile Cys Arg Lys Ala Arg Arg Leu Ala Gly Arg Gln Ala Glu
        40                  45                  50 ttg tgc cag gct gag ccg gaa gtg gtg gca gag cta gct cgg ggc gcc     306
Leu Cys Gln Ala Glu Pro Glu Val Val Ala Glu Leu Ala Arg Gly Ala
    55                  60                  65 cgg ctc ggg gtg cga gag tgc cag ttc cag ttc cgc ttc cgc cgc tgg     354
Arg Leu Gly Val Arg Glu Cys Gln Phe Gln Phe Arg Phe Arg Arg Trp
70                  75                  80                  85 aat tgc tcc agc cac agc aag gcc ttt gga cgc atc ctg caa cag gac     402
Asn Cys Ser Ser His Ser Lys Ala Phe Gly Arg Ile Leu Gln Gln Asp
                90                  95                  100 att cgg gag acg gcc ttc gtg ttc gcc atc act gcg gcc ggc gcc agc     450
Ile Arg Glu Thr Ala Phe Val Phe Ala Ile Thr Ala Ala Gly Ala Ser
            105                 110                 115
```

-continued

```
cac gcc gtc acg cag gcc tgt tct atg ggc gag ctg ctg cag tgc ggc      498
His Ala Val Thr Gln Ala Cys Ser Met Gly Glu Leu Leu Gln Cys Gly
        120                 125                 130 tgc cag gcg ccc cgc tgg cgg gcc cct ccc cgg ccc tcc ggc ctg ccc      546
Cys Gln Ala Pro Arg Trp Arg Ala Pro Pro Arg Pro Ser Gly Leu Pro
    135                 140                 145 ggc acc ccc gga ccc cct ggc ccc gcg ggc tcc ccg gaa ggc agc gcc      594
Gly Thr Pro Gly Pro Pro Gly Pro Ala Gly Ser Pro Glu Gly Ser Ala
150                 155                 160                 165 gcc tgg gag tgg gga ggc tgc ggc gac gac gtg gac ttc ggg gac gag      642
Ala Trp Glu Trp Gly Gly Cys Gly Asp Asp Val Asp Phe Gly Asp Glu
                170                 175                 180 aag tcg agg ctc ttt atg gac gcg cgg cac aag cgg gga cgc gga gac      690
Lys Ser Arg Leu Phe Met Asp Ala Arg His Lys Arg Gly Arg Gly Asp
            185                 190                 195 atc cgc gcg ttg gtg caa ctg cac aac aac gag gcg ggc agg ctg gcc      738
Ile Arg Ala Leu Val Gln Leu His Asn Asn Glu Ala Gly Arg Leu Ala
        200                 205                 210 gtg cgg agc cac acg cgc acc gag tgc aaa tgc cac ggg ctg tcg gga      786
Val Arg Ser His Thr Arg Thr Glu Cys Lys Cys His Gly Leu Ser Gly
    215                 220                 225 tca tgc gcg ctg cgc acc tgc tgg cag aag ctg cct cca ttt cgc gag      834
Ser Cys Ala Leu Arg Thr Cys Trp Gln Lys Leu Pro Pro Phe Arg Glu
230                 235                 240                 245 gtg ggc gcg cgg ctg ctg gag cgc ttc cac ggc gcc tca cgc gtc atg      882
Val Gly Ala Arg Leu Leu Glu Arg Phe His Gly Ala Ser Arg Val Met
                250                 255                 260 ggc acc aac gac ggc aag gcc ctg ctg ccc gcc gtc cgc acg ctc aag      930
Gly Thr Asn Asp Gly Lys Ala Leu Leu Pro Ala Val Arg Thr Leu Lys
            265                 270                 275 ccg ccg ggc cga gcg gac ctc ctc tac gcc gcc gat tcg ccc gac ttc      978
Pro Pro Gly Arg Ala Asp Leu Leu Tyr Ala Ala Asp Ser Pro Asp Phe
        280                 285                 290 tgc gcc ccc aac cga cgc acc ggc tcc ccc ggc acg cgc ggt cgc gcc     1026
Cys Ala Pro Asn Arg Arg Thr Gly Ser Pro Gly Thr Arg Gly Arg Ala
    295                 300                 305 tgc aat agc agc gcc ccg gac ctc agc ggc tgc gac ctg ctg tgc tgc     1074
Cys Asn Ser Ser Ala Pro Asp Leu Ser Gly Cys Asp Leu Leu Cys Cys
310                 315                 320                 325 ggc cgc ggg cac cgc cag gag agc gtg cag ctc gaa gag aac tgc ctg     1122
Gly Arg Gly His Arg Gln Glu Ser Val Gln Leu Glu Glu Asn Cys Leu
                330                 335                 340 tgc cgc ttc cac tgg tgc tgc gta gta cag tgc cac cgc tgc cgt gtg     1170
Cys Arg Phe His Trp Cys Cys Val Val Gln Cys His Arg Cys Arg Val
            345                 350                 355 cgc aag gag ctc agc ctc tgc ctg tgacccgccg cccggccgct agactgactt    1224
Arg Lys Glu Leu Ser Leu Cys Leu
        360                 365 cgcgcagcgg tggctcgcac ctgtgggacc tcagggcacc ggcaccgggc gcctctcgcc   1284
gctcgagccc agcctctccc tgccaaagcc caactcccag ggctctggaa atggtgaggc   1344
gaggggcttg agaggaacgc ccacccacga aggcccaggg cgccagacgg ccccgaaaag   1404
gcgctcgggg agcgtttaaa ggacactgta caggccctcc ctccccttgg cctctaggag   1464
gaaacagttt tttagactgg aaaaaagcca gtctaaaggc ctctggatac tgggctcccc   1524
agaactgctg gccacaggat ggtgggtgag gttagtatca ataaagatat ttaaaccacc   1584
```

<210> SEQ ID NO 6

<211> LENGTH: 365
<212> TYPE: PRT
<213> ORGANISM: Homo sapiens

<400> SEQUENCE: 6

```
Met Leu Pro Pro Leu Pro Ser Arg Leu Gly Leu Leu Leu Leu Leu Leu
1               5                   10                  15

Leu Cys Pro Ala His Val Gly Gly Leu Trp Trp Ala Val Gly Ser Pro
            20                  25                  30

Leu Val Met Asp Pro Thr Ser Ile Cys Arg Lys Ala Arg Arg Leu Ala
                35                  40                  45

Gly Arg Gln Ala Glu Leu Cys Gln Ala Glu Pro Val Val Ala Glu
    50                  55                  60

Leu Ala Arg Gly Ala Arg Leu Gly Val Arg Glu Cys Gln Phe Gln Phe
65                  70                  75                  80

Arg Phe Arg Arg Trp Asn Cys Ser Ser His Ser Lys Ala Phe Gly Arg
                85                  90                  95

Ile Leu Gln Gln Asp Ile Arg Glu Thr Ala Phe Val Phe Ala Ile Thr
                100                 105                 110

Ala Ala Gly Ala Ser His Ala Val Thr Gln Ala Cys Ser Met Gly Glu
            115                 120                 125

Leu Leu Gln Cys Gly Cys Gln Ala Pro Arg Trp Arg Ala Pro Pro Arg
130                 135                 140

Pro Ser Gly Leu Pro Gly Thr Pro Gly Pro Pro Gly Pro Ala Gly Ser
145                 150                 155                 160

Pro Glu Gly Ser Ala Ala Trp Glu Trp Gly Gly Cys Gly Asp Asp Val
                165                 170                 175

Asp Phe Gly Asp Glu Lys Ser Arg Leu Phe Met Asp Ala Arg His Lys
            180                 185                 190

Arg Gly Arg Gly Asp Ile Arg Ala Leu Val Gln Leu His Asn Asn Glu
        195                 200                 205

Ala Gly Arg Leu Ala Val Arg Ser His Thr Arg Thr Glu Cys Lys Cys
210                 215                 220

His Gly Leu Ser Gly Ser Cys Ala Leu Arg Thr Cys Trp Gln Lys Leu
225                 230                 235                 240

Pro Pro Phe Arg Glu Val Gly Ala Arg Leu Leu Glu Arg Phe His Gly
                245                 250                 255

Ala Ser Arg Val Met Gly Thr Asn Asp Gly Lys Ala Leu Leu Pro Ala
            260                 265                 270

Val Arg Thr Leu Lys Pro Pro Gly Arg Ala Asp Leu Leu Tyr Ala Ala
        275                 280                 285

Asp Ser Pro Asp Phe Cys Ala Pro Asn Arg Arg Thr Gly Ser Pro Gly
    290                 295                 300

Thr Arg Gly Arg Ala Cys Asn Ser Ser Ala Pro Asp Leu Ser Gly Cys
305                 310                 315                 320

Asp Leu Leu Cys Cys Gly Arg Gly His Arg Gln Glu Ser Val Gln Leu
                325                 330                 335

Glu Glu Asn Cys Leu Cys Arg Phe His Trp Cys Cys Val Val Gln Cys
            340                 345                 350

His Arg Cys Arg Val Arg Lys Glu Leu Ser Leu Cys Leu
        355                 360                 365
```

<210> SEQ ID NO 7
<211> LENGTH: 3017
<212> TYPE: DNA

```
<213> ORGANISM: Homo sapiens
<220> FEATURE:
<221> NAME/KEY: CDS
<222> LOCATION: (141)..(1343)
<223> OTHER INFORMATION:

<400> SEQUENCE: 7
gctgggcgca cggcgcggag ccggccggag ctcgaggccg gcggcggcgg gagagcgacc      60
cgggcggcct cgtagcgggg ccccggatcc ccgagtggcg gccggagcct cgaaaagaga     120
ttctcagcgc tgattttgag atg atg ggc ttg gga aac ggg cgt cgc agc atg    173
                      Met Met Gly Leu Gly Asn Gly Arg Arg Ser Met
                        1               5                  10 aag tcg ccg ccc ctc gtg ctg gcc gcc ctg gtg gcc tgc atc atc gtc      221
Lys Ser Pro Pro Leu Val Leu Ala Ala Leu Val Ala Cys Ile Ile Val
             15                  20                  25 ttg ggc ttc aac tac tgg att gcg agc tcc cgg agc gtg gac ctc cag      269
Leu Gly Phe Asn Tyr Trp Ile Ala Ser Ser Arg Ser Val Asp Leu Gln
         30                  35                  40 aca cgg atc atg gag ctg gaa ggc agg gtc cgc agg gcg gct gca gag      317
Thr Arg Ile Met Glu Leu Glu Gly Arg Val Arg Arg Ala Ala Ala Glu
     45                  50                  55 aga ggc gcc gtg gag ctg aag aag aac gag ttc cag gga gag ctg gag      365
Arg Gly Ala Val Glu Leu Lys Lys Asn Glu Phe Gln Gly Glu Leu Glu
 60                  65                  70                  75 aag cag cgg gag cag ctt gac aaa atc cag tcc agc cac aac ttc cag      413
Lys Gln Arg Glu Gln Leu Asp Lys Ile Gln Ser Ser His Asn Phe Gln
                 80                  85                  90 ctg gag agc gtc aac aag ctg tac cag gac gaa aag gcg gtt ttg gtg      461
Leu Glu Ser Val Asn Lys Leu Tyr Gln Asp Glu Lys Ala Val Leu Val
             95                 100                 105 aat aac atc acc aca ggt gag agg ctc atc cga gtg ctg caa gac cag      509
Asn Asn Ile Thr Thr Gly Glu Arg Leu Ile Arg Val Leu Gln Asp Gln
         110                 115                 120 tta aag acc ctg cag agg aat tac ggc agg ctg cag cag gat gtc ctc      557
Leu Lys Thr Leu Gln Arg Asn Tyr Gly Arg Leu Gln Gln Asp Val Leu
     125                 130                 135 cag ttt cag aag aac cag acc aac ctg gag agg aag ttc tcc tac gac      605
Gln Phe Gln Lys Asn Gln Thr Asn Leu Glu Arg Lys Phe Ser Tyr Asp
140                 145                 150                 155 ctg agc cag tgc atc aat cag atg aag gag gtg aag gaa cag tgt gag      653
Leu Ser Gln Cys Ile Asn Gln Met Lys Glu Val Lys Glu Gln Cys Glu
                 160                 165                 170 gag cga ata gaa gag gtc acc aaa aag ggg aat gaa gct gta gct tcc      701
Glu Arg Ile Glu Glu Val Thr Lys Lys Gly Asn Glu Ala Val Ala Ser
             175                 180                 185 aga gac ctg agt gaa aac aac gac cag aga cag cag ctc caa gcc ctc      749
Arg Asp Leu Ser Glu Asn Asn Asp Gln Arg Gln Gln Leu Gln Ala Leu
         190                 195                 200 agt gag cct cag ccc agg ctg cag gca gca ggc ctg cca cac aca gag      797
Ser Glu Pro Gln Pro Arg Leu Gln Ala Ala Gly Leu Pro His Thr Glu
     205                 210                 215 gtg cca caa ggg aag gga aac gtg ctt ggt aac agc aag tcc cag aca      845
Val Pro Gln Gly Lys Gly Asn Val Leu Gly Asn Ser Lys Ser Gln Thr
220                 225                 230                 235 cca gcc ccc agt tcc gaa gtg gtt ttg gat tca aag aga caa gtt gag      893
Pro Ala Pro Ser Ser Glu Val Val Leu Asp Ser Lys Arg Gln Val Glu
                 240                 245                 250 aaa gag gaa acc aat gag atc cag gtg gtg aat gag gag cct cag agg      941
Lys Glu Glu Thr Asn Glu Ile Gln Val Val Asn Glu Glu Pro Gln Arg
             255                 260                 265
```

| | |
|---|---|
| gac agg ctg ccg cag gag cca ggc cgg gag cag gtg gtg gaa gac aga<br>Asp Arg Leu Pro Gln Glu Pro Gly Arg Glu Gln Val Val Glu Asp Arg<br>270                 275                 280 | 989 |
| cct gta ggt gga aga ggc ttc ggg gga gcc gga gaa ctg ggc cag acc<br>Pro Val Gly Gly Arg Gly Phe Gly Gly Ala Gly Glu Leu Gly Gln Thr<br>285                 290                 295 | 1037 |
| cca cag gtg cag gct gcc ctg tca gtg agc cag gaa aat cca gag atg<br>Pro Gln Val Gln Ala Ala Leu Ser Val Ser Gln Glu Asn Pro Glu Met<br>300                 305                 310                 315 | 1085 |
| gag ggc cct gag cga gac cag ctt gtc atc ccc gac gga cag gag gag<br>Glu Gly Pro Glu Arg Asp Gln Leu Val Ile Pro Asp Gly Gln Glu Glu<br>                320                 325                 330 | 1133 |
| gag cag gaa gct gcc ggg gaa ggg aga aac cag cag aaa ctg aga gga<br>Glu Gln Glu Ala Ala Gly Glu Gly Arg Asn Gln Gln Lys Leu Arg Gly<br>                335                 340                 345 | 1181 |
| gaa gat gac tac aac atg gat gaa aat gaa gca gaa tct gag aca gac<br>Glu Asp Asp Tyr Asn Met Asp Glu Asn Glu Ala Glu Ser Glu Thr Asp<br>350                 355                 360 | 1229 |
| aag caa gca gcc ctg gca ggg aat gac aga aac ata gat gtt ttt aat<br>Lys Gln Ala Ala Leu Ala Gly Asn Asp Arg Asn Ile Asp Val Phe Asn<br>365                 370                 375 | 1277 |
| gtt gaa gat cag aaa aga gac acc ata aat tta ctt gat cag cgt gaa<br>Val Glu Asp Gln Lys Arg Asp Thr Ile Asn Leu Leu Asp Gln Arg Glu<br>380                 385                 390                 395 | 1325 |
| aag cgg aat cat aca ctc tgaattgaac tggaatcaca tatttcacaa<br>Lys Arg Asn His Thr Leu<br>                400 | 1373 |
| cagggccgaa gagatgactt taaaatgttc atgagggact gaatactgaa aactgtgaaa | 1433 |
| tgtactaaat aaaatgtaca tctgaagatg attattgtga aattttagta tgcactttgt | 1493 |
| gtaggaaaaa atggaatggt cttttaaaca gcttttgggg ggtactttgg aagtgtctaa | 1553 |
| taaggtgtca caattttttgg tagtaggtat ttcgtgagaa gctcaacacc aaaactggaa | 1613 |
| catagttctc cttcaagtgt tggcgacagc ggggcttcct gattctggaa tataactttg | 1673 |
| tgtaaattaa cagccaccta tagaagagtc catctgctgt gaaggagaga cagagaactc | 1733 |
| tgggttccgt cgtcctgtcc acgtgctgta ccaagtgctg gtgccagcct gttacctgtt | 1793 |
| ctcactgaaa agtctggcta atgctcttgt gtagtcactt ctgattctga caatcaatca | 1853 |
| atcaatggcc tagagcactg actgttaaca caaacgtcac tagcaaagta gcaacagctt | 1913 |
| taagtctaaa tacaaagctg ttctgtgtga gaattttttta aaaggctact tgtataataa | 1973 |
| cccttgtcat ttttaatgta caaaacgcta ttaagtggct tagaatttga acatttgtgg | 2033 |
| tctttattta ctttgcttcg tgtgtgggca aagcaacatc ttccctaaat atatattacc | 2093 |
| aagaaaagca agaagcagat taggttttttg acaaaacaaa caggccaaaa gggggctgac | 2153 |
| ctggagcaga gcatggtgag aggcaaggca tgagagggca gttttgttg tggacagatc | 2213 |
| tgtgcctact ttattactgg agtaaaagaa aacaaagttc attgatgtcg aaggatatat | 2273 |
| acagtgttag aaattaggac tgtttagaaa aacaggaata caatggttgt ttttatcata | 2333 |
| gtgtacacat ttagcttgtg gtaaatgact cacaaaactg attttaaaat caagttaatg | 2393 |
| tgaattttga aaattactac ttaatcctaa ttcacaataa caatggcatt aaggtttgac | 2453 |
| ttgagttggt tcttagtatt atttatggta aataggctct taccacttgc aaataactgg | 2513 |
| ccacatcatt aatgactgac ttcccagtaa ggctctctaa ggggtaagta ggaggatcca | 2573 |
| caggatttga gatgctaagg ccccagagat cgtttgaacc aaccctctta ttttcagagg | 2633 |

```
ggaaaatggg gcctagaagt tacagagcat ctagctggtg cgctggcacc cctggcctca   2693
cacagactcc cgagtagctg ggactacagg cacacagtca ctgaagcagg ccctgtttgc   2753
aattcacgct gccacctcca acttaaacat tcttcatatg tgatgtcctt agtcactaag   2813
gttaaacttt cccacccaga aaaggcaact tagataaaat cttagagtac tttcatactc   2873
ttctaagtcc tcttccagcc tcactttgag tcctccttgg ggttgatagg aattttctct   2933
tgctttctca ataaagtctc tattcatctc atgtttaatt tgtacgcata gaattgctga   2993
gaaataaaat gttctgttca actt                                          3017
```

<210> SEQ ID NO 8
<211> LENGTH: 401
<212> TYPE: PRT
<213> ORGANISM: Homo sapiens

<400> SEQUENCE: 8

```
Met Met Gly Leu Gly Asn Gly Arg Arg Ser Met Lys Ser Pro Pro Leu
  1               5                  10                  15

Val Leu Ala Ala Leu Val Ala Cys Ile Ile Val Leu Gly Phe Asn Tyr
             20                  25                  30

Trp Ile Ala Ser Ser Arg Ser Val Asp Leu Gln Thr Arg Ile Met Glu
         35                  40                  45

Leu Glu Gly Arg Val Arg Arg Ala Ala Ala Glu Arg Gly Ala Val Glu
     50                  55                  60

Leu Lys Lys Asn Glu Phe Gln Gly Glu Leu Glu Lys Gln Arg Glu Gln
 65                  70                  75                  80

Leu Asp Lys Ile Gln Ser Ser His Asn Phe Gln Leu Glu Ser Val Asn
                 85                  90                  95

Lys Leu Tyr Gln Asp Glu Lys Ala Val Leu Val Asn Asn Ile Thr Thr
            100                 105                 110

Gly Glu Arg Leu Ile Arg Val Leu Gln Asp Gln Leu Lys Thr Leu Gln
        115                 120                 125

Arg Asn Tyr Gly Arg Leu Gln Gln Asp Val Leu Gln Phe Gln Lys Asn
    130                 135                 140

Gln Thr Asn Leu Glu Arg Lys Phe Ser Tyr Asp Leu Ser Gln Cys Ile
145                 150                 155                 160

Asn Gln Met Lys Glu Val Lys Glu Gln Cys Glu Glu Arg Ile Glu Glu
                165                 170                 175

Val Thr Lys Lys Gly Asn Glu Ala Val Ala Ser Arg Asp Leu Ser Glu
            180                 185                 190

Asn Asn Asp Gln Arg Gln Gln Leu Gln Ala Leu Ser Glu Pro Gln Pro
        195                 200                 205

Arg Leu Gln Ala Ala Gly Leu Pro His Thr Glu Val Pro Gln Gly Lys
    210                 215                 220

Gly Asn Val Leu Gly Asn Ser Lys Ser Gln Thr Pro Ala Pro Ser Ser
225                 230                 235                 240

Glu Val Val Leu Asp Ser Lys Arg Gln Val Glu Lys Glu Glu Thr Asn
                245                 250                 255

Glu Ile Gln Val Val Asn Glu Glu Pro Gln Arg Asp Arg Leu Pro Gln
            260                 265                 270

Glu Pro Gly Arg Glu Gln Val Val Glu Asp Arg Pro Val Gly Gly Arg
        275                 280                 285

Gly Phe Gly Gly Ala Gly Glu Leu Gly Gln Thr Pro Gln Val Gln Ala
    290                 295                 300
```

-continued

| | | | | | | | | | | | |
|---|---|---|---|---|---|---|---|---|---|---|---|
| Ala | Leu | Ser | Val | Ser | Gln | Glu | Asn | Pro | Glu | Met | Glu | Gly | Pro | Glu | Arg |
| 305 | | | | 310 | | | | | 315 | | | | | 320 | |

| Asp | Gln | Leu | Val | Ile | Pro | Asp | Gly | Gln | Glu | Glu | Gln | Glu | Ala | Ala |
|---|---|---|---|---|---|---|---|---|---|---|---|---|---|---|
| | | | | 325 | | | | | 330 | | | | | 335 |

| Gly | Glu | Gly | Arg | Asn | Gln | Gln | Lys | Leu | Arg | Gly | Glu | Asp | Tyr | Asn |
|---|---|---|---|---|---|---|---|---|---|---|---|---|---|---|
| | | | 340 | | | | | 345 | | | | 350 | | |

| Met | Asp | Glu | Asn | Glu | Ala | Glu | Ser | Glu | Thr | Asp | Lys | Gln | Ala | Ala | Leu |
|---|---|---|---|---|---|---|---|---|---|---|---|---|---|---|---|
| | | 355 | | | | | 360 | | | | | 365 | | | |

| Ala | Gly | Asn | Asp | Arg | Asn | Ile | Asp | Val | Phe | Asn | Val | Glu | Asp | Gln | Lys |
|---|---|---|---|---|---|---|---|---|---|---|---|---|---|---|---|
| | 370 | | | | | 375 | | | | | 380 | | | | |

| Arg | Asp | Thr | Ile | Asn | Leu | Leu | Asp | Gln | Arg | Glu | Lys | Arg | Asn | His | Thr |
|---|---|---|---|---|---|---|---|---|---|---|---|---|---|---|---|
| 385 | | | | | 390 | | | | | 395 | | | | | 400 |

Leu

<210> SEQ ID NO 9
<211> LENGTH: 3520
<212> TYPE: DNA
<213> ORGANISM: Homo sapiens
<220> FEATURE:
<221> NAME/KEY: CDS
<222> LOCATION: (40)..(1875)
<223> OTHER INFORMATION:

<400> SEQUENCE: 9

```
gaaattcagg ttaacgccat tgataaaggg attccttcc atg gca ggt cac agc         54
                                            Met Ala Gly His Ser
                                              1               5 atg gtc ctg gtg gaa att ctg gac gtg aat gac aat gtc cct gaa gta       102
Met Val Leu Val Glu Ile Leu Asp Val Asn Asp Asn Val Pro Glu Val
                10                  15                  20 atg gtt act tca ctg tcg ctc cct gtg caa gag gat gct cag gtg ggt       150
Met Val Thr Ser Leu Ser Leu Pro Val Gln Glu Asp Ala Gln Val Gly
            25                  30                  35 acc gtc att gcc ctg att agc gtg tcg gat cgt gac tct gga gcc aat       198
Thr Val Ile Ala Leu Ile Ser Val Ser Asp Arg Asp Ser Gly Ala Asn
        40                  45                  50 gga cag gtc atc tgc tca ctg aca cct cat gtt ccc ttc aag ctg gtg       246
Gly Gln Val Ile Cys Ser Leu Thr Pro His Val Pro Phe Lys Leu Val
    55                  60                  65 tcc acc tac aag aat tac tac tcg ttg gtg ctg gac agc gcc ctg gac       294
Ser Thr Tyr Lys Asn Tyr Tyr Ser Leu Val Leu Asp Ser Ala Leu Asp
70                  75                  80                  85 cgc gag agc gtg tcg gcc tat gag ctg gtg gtg act gcg cgg gat ggg       342
Arg Glu Ser Val Ser Ala Tyr Glu Leu Val Val Thr Ala Arg Asp Gly
                90                  95                 100 ggc tcg cct tcg ctg tgg gcc acg gct aga gtg tcc gtg gag gtg gcc       390
Gly Ser Pro Ser Leu Trp Ala Thr Ala Arg Val Ser Val Glu Val Ala
            105                 110                 115 gac gtg aac gac aat gcg cct gcg ttc gcg cag ccc gag tac aca gtg       438
Asp Val Asn Asp Asn Ala Pro Ala Phe Ala Gln Pro Glu Tyr Thr Val
        120                 125                 130 ttc gtg aag gag aac aac ccg ccg ggc tgc cac atc ttc acg gtg tcg       486
Phe Val Lys Glu Asn Asn Pro Pro Gly Cys His Ile Phe Thr Val Ser
    135                 140                 145 gca tgg gac gcg gac gcg cag aag aac gcg ctg gtg tcc tac tcg ctg       534
Ala Trp Asp Ala Asp Ala Gln Lys Asn Ala Leu Val Ser Tyr Ser Leu
150                 155                 160                 165 gtg gag cgg cgg gtg ggc gag cac gca ctg tcg agc tac gtg tcg gtg       582
Val Glu Arg Arg Val Gly Glu His Ala Leu Ser Ser Tyr Val Ser Val
                170                 175                 180
```

```
cac gcg gag agc ggc aag gtg tac gcg ctg cag ccg cta gac cac gag      630
His Ala Glu Ser Gly Lys Val Tyr Ala Leu Gln Pro Leu Asp His Glu
            185                 190                 195 gag ctg gag ctg ctg cag ttc cag gtg agc gcg cgc gac gcc ggc gtg      678
Glu Leu Glu Leu Leu Gln Phe Gln Val Ser Ala Arg Asp Ala Gly Val
                200                 205                 210 ccg cct ctg ggc agc aac gtg acg ctg cag gtg ttc gtg ctg gac gag      726
Pro Pro Leu Gly Ser Asn Val Thr Leu Gln Val Phe Val Leu Asp Glu
        215                 220                 225 aac gac aac gcg ccg gca ctg ctg gcg act ccg gct ggc agc gca gga      774
Asn Asp Asn Ala Pro Ala Leu Leu Ala Thr Pro Ala Gly Ser Ala Gly
230                 235                 240                 245 ggc gca gtt agc gag ttg gta ccg cgg tcg gtg ggt gcg ggc cac gtg      822
Gly Ala Val Ser Glu Leu Val Pro Arg Ser Val Gly Ala Gly His Val
            250                 255                 260 gtg gcg aaa gtg cgc gcg gtg gac gct gac tcc ggc tat aac gct tgg      870
Val Ala Lys Val Arg Ala Val Asp Ala Asp Ser Gly Tyr Asn Ala Trp
                265                 270                 275 ctg tcc tac gag ttg caa ccg gcg gcg gtc ggc gcg cac atc ccg ttc      918
Leu Ser Tyr Glu Leu Gln Pro Ala Ala Val Gly Ala His Ile Pro Phe
        280                 285                 290 cac gtg ggg ctg tac act ggc gag atc agc acg aca cgc atc ctg gat      966
His Val Gly Leu Tyr Thr Gly Glu Ile Ser Thr Thr Arg Ile Leu Asp
295                 300                 305 gag gcg gac gct ccg cgc cac cgc ctg ctg gtg ctg gtg aag gac cac     1014
Glu Ala Asp Ala Pro Arg His Arg Leu Leu Val Leu Val Lys Asp His
310                 315                 320                 325 ggt gag ccc gcg ctg acg tcc acg gcc acg gtg ctg gtg tcg ctg gtg     1062
Gly Glu Pro Ala Leu Thr Ser Thr Ala Thr Val Leu Val Ser Leu Val
            330                 335                 340 gag aac ggc cag gcc cca aag acg tcg tcg cgg gcc tca gtg ggc gct     1110
Glu Asn Gly Gln Ala Pro Lys Thr Ser Ser Arg Ala Ser Val Gly Ala
                345                 350                 355 gtg gat ccc gaa gcg gct ctg gtg gat att aac gtg tac ctc atc atc     1158
Val Asp Pro Glu Ala Ala Leu Val Asp Ile Asn Val Tyr Leu Ile Ile
        360                 365                 370 gcc atc tgt gcg gtg tcc agc ctg ctg gtg ctc acg ctg ctg ttg tac     1206
Ala Ile Cys Ala Val Ser Ser Leu Leu Val Leu Thr Leu Leu Leu Tyr
375                 380                 385 act gcg ctg cgt tgc tca gcg ccg ccc acc gtg agc cgg tgc gcg ccg     1254
Thr Ala Leu Arg Cys Ser Ala Pro Pro Thr Val Ser Arg Cys Ala Pro
390                 395                 400                 405 ggc aag ccc acg ctg gtg tgc tcc agc gcc gtg ggg agt tgg tct tac     1302
Gly Lys Pro Thr Leu Val Cys Ser Ser Ala Val Gly Ser Trp Ser Tyr
            410                 415                 420 tcg cag cag agg agg cag agg gtg tgc tct gca gag agc ccg ccc aag     1350
Ser Gln Gln Arg Arg Gln Arg Val Cys Ser Ala Glu Ser Pro Pro Lys
                425                 430                 435 acg gac ctc atg gcc ttc agc cca agc ctt cag ctg tct cga gaa gat     1398
Thr Asp Leu Met Ala Phe Ser Pro Ser Leu Gln Leu Ser Arg Glu Asp
        440                 445                 450 tgt tta aat cct ccc agt gaa cca cga cag ccc aac cct gac tgg cgt     1446
Cys Leu Asn Pro Pro Ser Glu Pro Arg Gln Pro Asn Pro Asp Trp Arg
455                 460                 465 tac tct gcc tcc ctg aga gca ggc atg cac agc tct gtg cac cta gag     1494
Tyr Ser Ala Ser Leu Arg Ala Gly Met His Ser Ser Val His Leu Glu
470                 475                 480                 485 gag gct ggc att cta cgg gct ggt cca gga ggg cct gat cag cag tgg     1542
Glu Ala Gly Ile Leu Arg Ala Gly Pro Gly Gly Pro Asp Gln Gln Trp
```

-continued

|  |  |  |  |  |  |  |  |  |  |  |  |
|---|---|---|---|---|---|---|---|---|---|---|---|
| 490 | | | | 495 | | | | 500 | | | |

| cca | aca | gta | tcc | agt | gca | aca | cca | gaa | cca | gag | gca | gga | gaa | gtg | tcc | 1590 |
| Pro | Thr | Val | Ser | Ser | Ala | Thr | Pro | Glu | Pro | Glu | Ala | Gly | Glu | Val | Ser | |
| | | | 505 | | | | | 510 | | | | | 515 | | | |

| cct | cca | gtc | ggt | gcg | ggt | gtc | aac | agc | aac | agc | tgg | acc | ttt | aaa | tac | 1638 |
| Pro | Pro | Val | Gly | Ala | Gly | Val | Asn | Ser | Asn | Ser | Trp | Thr | Phe | Lys | Tyr | |
| | | | 520 | | | | | 525 | | | | | 530 | | | |

| gga | cca | ggc | aac | ccc | aaa | caa | tcc | ggt | ccc | ggt | gag | ttg | ccc | gac | aaa | 1686 |
| Gly | Pro | Gly | Asn | Pro | Lys | Gln | Ser | Gly | Pro | Gly | Glu | Leu | Pro | Asp | Lys | |
| | | | 535 | | | | | 540 | | | | | 545 | | | |

| ttc | att | atc | cca | gga | tct | cct | gca | atc | atc | tcc | atc | cgg | cag | gag | cct | 1734 |
| Phe | Ile | Ile | Pro | Gly | Ser | Pro | Ala | Ile | Ile | Ser | Ile | Arg | Gln | Glu | Pro | |
| 550 | | | | | 555 | | | | | 560 | | | | | 565 | |

| act | aac | agc | caa | att | gac | aaa | agt | gac | ttc | ata | acc | ttc | ggc | aaa | aag | 1782 |
| Thr | Asn | Ser | Gln | Ile | Asp | Lys | Ser | Asp | Phe | Ile | Thr | Phe | Gly | Lys | Lys | |
| | | | | 570 | | | | | 575 | | | | | 580 | | |

| gag | gag | acc | aag | aaa | aag | aag | aaa | aag | aag | aag | ggt | aac | aag | acc | cag | 1830 |
| Glu | Glu | Thr | Lys | Lys | Lys | Lys | Lys | Lys | Lys | Lys | Gly | Asn | Lys | Thr | Gln | |
| | | | | 585 | | | | | 590 | | | | | 595 | | |

| gag | aaa | aaa | gag | aaa | ggg | aac | agc | acg | act | gac | aac | agt | gac | cag | | 1875 |
| Glu | Lys | Lys | Glu | Lys | Gly | Asn | Ser | Thr | Thr | Asp | Asn | Ser | Asp | Gln | | |
| | | | 600 | | | | | 605 | | | | | 610 | | | |

| tgaggtcctc | aaatggaaac | aagccactta | gccagttttt | gtaataatgg | caaatctctc | 1935 |
| ccatgtagca | attccctgct | cctttttcct | atctacatga | gccctcttag | agacctcaga | 1995 |
| aatctgcaga | aagttccctg | tgtctgtcta | gaacgcattt | aacaggtttt | gtcgtaaaag | 2055 |
| ctttactaag | tctggtgtta | actctttctc | tccactctgg | cttgttttca | gaacctaaaa | 2115 |
| agcagaccca | agtttccttt | ctcctccgcc | gcaaaggaga | ggcttcccag | ccccgccagt | 2175 |
| gagaggttgg | actctctgcc | ctgtgctccg | gggatcctgt | cttgatgaca | cttgcagggc | 2235 |
| aggctgaaaa | gttttgagat | tgagcagctt | gggagtttgt | ggccactggg | tatgtgtagc | 2295 |
| taccgcgggt | atgcgagtgc | cagatattgg | ctgagacgag | ccagcttaga | ctaattggta | 2355 |
| caaggaaggc | aagaaaacaa | agacaaataa | acagcggaag | ttatcagtat | ggaggggaag | 2415 |
| tgtaaactta | aagggaccag | actttctaaa | tcttacaact | caagaggtgg | cagccaccct | 2475 |
| ctaggagaca | aaactacccc | cactgacaag | gctttaggag | accctaaagt | ctgttggctg | 2535 |
| tgacgtcatt | atacctaaaa | tctgcatcat | acctgcaagc | caacagttca | gtgttttaac | 2595 |
| agagaaccac | cctgggaaac | agaagcagat | ctgatgtgtt | tcctatacat | gtcctgtgct | 2655 |
| cactttatta | aaaattcttt | tgcacacaat | gtttatgaaa | aggccagatc | cttttccaat | 2715 |
| acttatgcaa | aagcaaaaga | aaaccccgac | acctcacctt | tcgctgtttg | ttgtttcata | 2775 |
| gatttattta | aaaaaagaga | aagtctatag | ctataaatct | ttaaagagaa | atatgaatac | 2835 |
| aattccccta | aactctcctc | aaaagagaat | tcagtctaca | gccatttaaa | tgatcattgc | 2895 |
| tgctacagaa | gtgctttaag | agaattgcct | gaaacatctg | tattatatcg | gccacctgcc | 2955 |
| aatcacagct | ttactctttc | aggtcactct | ggggctgcct | cttgcatgta | ttactaaata | 3015 |
| aaatgatctc | tctttctctc | tctctctctc | ttttctaaga | aacaattatg | tgcactttga | 3075 |
| tacacaacct | tctctaacca | actatatatc | aagacccaaa | aattgaagaa | aaatattgtt | 3135 |
| ttctcataca | gtgagcggat | ttttcaatct | actaattctg | tgacttgtct | tggtgtgcta | 3195 |
| gcctacacct | tctctttggt | ttagttttcc | ttttctataa | cactctgaat | tgctaatctt | 3255 |
| actaacacct | atgatgttac | ctgaaatcaa | tctcccatat | gtatgctgta | tgctatgcta | 3315 |
| agactcctga | aatatactta | ctctgtgctt | gtgtatgtga | atgttaatgc | aactattacc | 3375 |

```
tagagtgaac tttaagcttt attgttgaat gtaattccat tatatttcct tttgtacacc    3435
tgtgaaaaag tggagtagtg ttttttttaac cattgttaat cagcttttgt gtatgaaaga   3495
cacagtaaaa tttctttctt aaatc                                          3520
```

<210> SEQ ID NO 10
<211> LENGTH: 612
<212> TYPE: PRT
<213> ORGANISM: Homo sapiens

<400> SEQUENCE: 10

```
Met Ala Gly His Ser Met Val Leu Val Glu Ile Leu Asp Val Asn Asp
1               5                   10                  15

Asn Val Pro Glu Val Met Val Thr Ser Leu Ser Leu Pro Val Gln Glu
            20                  25                  30

Asp Ala Gln Val Gly Thr Val Ile Ala Leu Ile Ser Val Ser Asp Arg
        35                  40                  45

Asp Ser Gly Ala Asn Gly Gln Val Ile Cys Ser Leu Thr Pro His Val
    50                  55                  60

Pro Phe Lys Leu Val Ser Thr Tyr Lys Asn Tyr Ser Leu Val Leu
65                  70                  75                  80

Asp Ser Ala Leu Asp Arg Glu Ser Val Ser Ala Tyr Glu Leu Val Val
                85                  90                  95

Thr Ala Arg Asp Gly Gly Ser Pro Ser Leu Trp Ala Thr Ala Arg Val
            100                 105                 110

Ser Val Glu Val Ala Asp Val Asn Asp Asn Ala Pro Ala Phe Ala Gln
        115                 120                 125

Pro Glu Tyr Thr Val Phe Val Lys Glu Asn Asn Pro Gly Cys His
    130                 135                 140

Ile Phe Thr Val Ser Ala Trp Asp Ala Asp Ala Gln Lys Asn Ala Leu
145                 150                 155                 160

Val Ser Tyr Ser Leu Val Glu Arg Arg Val Gly Glu His Ala Leu Ser
                165                 170                 175

Ser Tyr Val Ser Val His Ala Glu Ser Gly Lys Val Tyr Ala Leu Gln
            180                 185                 190

Pro Leu Asp His Glu Glu Leu Glu Leu Leu Gln Phe Gln Val Ser Ala
        195                 200                 205

Arg Asp Ala Gly Val Pro Pro Leu Gly Ser Asn Val Thr Leu Gln Val
    210                 215                 220

Phe Val Leu Asp Glu Asn Asp Asn Ala Pro Ala Leu Leu Ala Thr Pro
225                 230                 235                 240

Ala Gly Ser Ala Gly Ala Val Ser Glu Leu Val Pro Arg Ser Val
                245                 250                 255

Gly Ala Gly His Val Val Ala Lys Val Arg Ala Val Asp Ala Asp Ser
            260                 265                 270

Gly Tyr Asn Ala Trp Leu Ser Tyr Glu Leu Gln Pro Ala Ala Val Gly
        275                 280                 285

Ala His Ile Pro Phe His Val Gly Leu Tyr Thr Gly Glu Ile Ser Thr
    290                 295                 300

Thr Arg Ile Leu Asp Glu Ala Asp Ala Pro Arg His Arg Leu Leu Val
305                 310                 315                 320

Leu Val Lys Asp His Gly Glu Pro Ala Leu Thr Ser Thr Ala Thr Val
                325                 330                 335

Leu Val Ser Leu Val Glu Asn Gly Gln Ala Pro Lys Thr Ser Ser Arg
```

-continued

```
                340             345             350
Ala Ser Val Gly Ala Val Asp Pro Glu Ala Ala Leu Val Asp Ile Asn
        355                 360                 365
Val Tyr Leu Ile Ile Ala Ile Cys Ala Val Ser Ser Leu Leu Val Leu
    370                 375                 380
Thr Leu Leu Leu Tyr Thr Ala Leu Arg Cys Ser Ala Pro Pro Thr Val
385                 390                 395                 400
Ser Arg Cys Ala Pro Gly Lys Pro Thr Leu Val Cys Ser Ser Ala Val
                405                 410                 415
Gly Ser Trp Ser Tyr Ser Gln Gln Arg Gln Arg Val Cys Ser Ala
            420                 425                 430
Glu Ser Pro Pro Lys Thr Asp Leu Met Ala Phe Ser Pro Ser Leu Gln
        435                 440                 445
Leu Ser Arg Glu Asp Cys Leu Asn Pro Pro Ser Glu Pro Arg Gln Pro
    450                 455                 460
Asn Pro Asp Trp Arg Tyr Ser Ala Ser Leu Arg Ala Gly Met His Ser
465                 470                 475                 480
Ser Val His Leu Glu Glu Ala Gly Ile Leu Arg Ala Gly Pro Gly Gly
                485                 490                 495
Pro Asp Gln Gln Trp Pro Thr Val Ser Ser Ala Thr Pro Glu Pro Glu
            500                 505                 510
Ala Gly Glu Val Ser Pro Pro Val Gly Ala Gly Val Asn Ser Asn Ser
        515                 520                 525
Trp Thr Phe Lys Tyr Gly Pro Gly Asn Pro Lys Gln Ser Gly Pro Gly
    530                 535                 540
Glu Leu Pro Asp Lys Phe Ile Ile Pro Gly Ser Pro Ala Ile Ile Ser
545                 550                 555                 560
Ile Arg Gln Glu Pro Thr Asn Ser Gln Ile Asp Lys Ser Asp Phe Ile
                565                 570                 575
Thr Phe Gly Lys Lys Glu Glu Thr Lys Lys Lys Lys Lys Lys
            580                 585                 590
Gly Asn Lys Thr Gln Glu Lys Lys Glu Lys Gly Asn Ser Thr Thr Asp
        595                 600                 605
Asn Ser Asp Gln
    610
```

<210> SEQ ID NO 11
<211> LENGTH: 30
<212> TYPE: RNA
<213> ORGANISM: Artificial Sequence
<220> FEATURE:
<223> OTHER INFORMATION: Synthetic oligo-cap linker

<400> SEQUENCE: 11
agcaucgagu cggccuuguu ggccuacugg        30

<210> SEQ ID NO 12
<211> LENGTH: 42
<212> TYPE: DNA
<213> ORGANISM: Artificial Sequence
<220> FEATURE:
<223> OTHER INFORMATION: Synthetic DNA

<400> SEQUENCE: 12
gcggctgaag acggcctatg tggcctttttt ttttttttt tt        42

<210> SEQ ID NO 13

```
<211> LENGTH: 21
<212> TYPE: DNA
<213> ORGANISM: Artificial Sequence
<220> FEATURE:
<223> OTHER INFORMATION: Synthetic DNA

<400> SEQUENCE: 13
agcatcgagt cggccttgtt g                                            21

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
gcggctgaag acggcctatg t                                            21

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
gtggatgcga tctgtctctc c                                            21

<210> SEQ ID NO 16
<211> LENGTH: 21
<212> TYPE: DNA
<213> ORGANISM: Artificial Sequence
<220> FEATURE:
<223> OTHER INFORMATION: Synthetic DNA

<400> SEQUENCE: 16
tgcagaaagg aacacatgct g                                            21

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
cttccatgct tcagctgtgg                                              20

<210> SEQ ID NO 18
<211> LENGTH: 21
<212> TYPE: DNA
<213> ORGANISM: Artificial Sequence
<220> FEATURE:
<223> OTHER INFORMATION: Synthetic DNA

<400> SEQUENCE: 18
gccctggtct gtatacctgg g                                            21

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

<400> SEQUENCE: 19
```

```
                                          -continued
ctacgacctg agccagtgca                                                      20

<210> SEQ ID NO 20
<211> LENGTH: 19
<212> TYPE: DNA
<213> ORGANISM: Artificial Sequence
<220> FEATURE:
<223> OTHER INFORMATION: Synthetic DNA

<400> SEQUENCE: 20
gagggcttgg agctgctgt                                                       19

<210> SEQ ID NO 21
<211> LENGTH: 19
<212> TYPE: DNA
<213> ORGANISM: Artificial Sequence
<220> FEATURE:
<223> OTHER INFORMATION: Synthetic DNA

<400> SEQUENCE: 21
gcattctacg ggctggtcc                                                       19

<210> SEQ ID NO 22
<211> LENGTH: 19
<212> TYPE: DNA
<213> ORGANISM: Artificial Sequence
<220> FEATURE:
<223> OTHER INFORMATION: Synthetic DNA

<400> SEQUENCE: 22
gggttgcctg gtccgtatt                                                       19
```

AMYLOID-β PROTEIN AGGREGATION-REGULATING FACTORS

TECHNICAL FIELD

The present invention relates to proteins that suppress or promote the aggregation or deposition of amyloid-β protein (also referred to as "Aβ" hereinafter), polynucleotides encoding the proteins, a method for preparing the proteins using the polynucleotides, an expression system for producing the proteins, and a method of screening for a compound that suppresses or promotes the aggregation of amyloid-β protein using the expression system. The present invention also relates to a method for preventing and treating Alzheimer's disease using proteins obtained by the method above, or a compound obtained by the screening method.

BACKGROUND ART

Alzheimer's disease is a disorder associated with cognitive dysfunctions, and is characterized by a loss of nerve cells and emergence of a large number of senile plaques and neurofibrillary tangles. Senile plaques are detected at the earliest stage of development of this disease. These plaques are highly specific to this disease since they are not found in other neurodegenerative disorders. Amyloid-β protein (Aβ) is the major constituent of senile plaques and forms amyloidfibrils having a β-sheet structure. Aβ is a polypeptide comprising approximately 40 amino acid residues and has a molecular weight of 4,000 Da. It easily aggregates to form fibrils and becomes insoluble. The major molecular species of this protein are Aβ40, which ends with valine at amino acid residue 40, and Aβ42, the longer form of Aβ having two additional residues. Although Aβ is usually degraded and never accumulates in the brain, the degrading capacity decreases with aging, causing an accumulation of Aβ. This triggers neuronal dysfunction and cell death, ultimately resulting in dementia and Alzheimer's disease. Through various genetic analyses and molecular biological and neuropharmacological studies, "amyloid hypothesis" has been proposed as a cause of the pathogenesis of Alzheimer's disease.

DISCLOSURE OF THE INVENTION

An objective of the present invention is to provide proteins that suppress or promote aggregation or deposition of amyloid-β protein, and polynucleotides encoding these proteins. A further objective of the present invention is to provide a method for treating Alzheimer's disease by discovering a method or substance that suppresses or promotes aggregation or deposition of amyloid-β protein.

To achieve the above objectives, the present inventors conducted extensive studies and finally discovered polynucleotides encoding secretory or membrane-bound forms of proteins that suppress or promote the aggregation or deposition of amyloid-β protein, and hence completed the present invention.

Thus, the present invention relates to:

[1] a polynucleotide encoding a protein that suppresses or promotes the aggregation or deposition of amyloid-β protein, wherein the polynucleotide is selected from the group consisting of:
  (a) a polynucleotide that comprises a nucleotide sequence as set forth in SEQ ID NO: 1, 3, 5, 7 or 9,
  (b) a polynucleotide that encodes a protein having a amino acid sequence as set forth in SEQ ID NO: 2, 4, 6, 8 or 10,
  (c) a polynucleotide that encodes a protein comprising an amino acid sequence in which one or several amino acids of the amino acid sequence of SEQ ID NO. 2, 4, 6, 8 or 10, have been substituted, deleted, inserted and/or added;
  (d) a polynucleotide that hybridizes under stringent conditions to a polynucleotide comprising a nucleotide sequence as set forth in SEQ ID NO. 1, 3, 5, 7 or 9; or,
  (e) a polynucleotide that shows at least (i) 60%, (ii) 70%, (iii) 80%, (iv) 90%, or (v) 95% homology to a nucleotide sequence as set forth in SEQ ID NO. 1, 3, 5, 7 or 9;

[2] a polynucleotide encoding a partial peptide of the protein encoded by a polynucleotide according to [1];

[3] a peptide or protein encoded by a polynucleotide according to [1] or [2];

[4] a protein that suppresses or promotes the aggregation of amyloid-β protein, wherein said protein is encoded by a polynucleotide that, from a molecular evolutionary aspect, originated from the same gene from which a polynucleotide according to [1] originated from;

[5] a vector comprising a polynucleotide according to [1] or [2];

[6] a transfectant harboring a polynucleotide according to [1] or [2] or the vector according to [5];

[7] a method for producing the peptide or protein according to [3], wherein said method comprises the steps of: culturing the transfectant according to [6], and recovering the expression product;

[8] a polynucleotide comprising a polynucleotide according to [1] or [2] or a nucleotide sequence complementary to the complementary strand of the polynucleotide according to [1] or [2], wherein said polynucleotide comprises at least 15 nucleotides;

[9] an antibody against the peptide or protein according to [3];

[10] an immunological assay comprising the step of: monitoring an immunological reaction between the peptide or protein according to [3] and the antibody according to [9];

[11] a method of screening for a compound that regulates the activity of a protein encoded by a polynucleotide according to [1], wherein said method comprises the following steps of:
  contacting a candidate compound with a protein encoded by a polynucleotide according to [1], or with a cell expressing said protein, in the presence of amyloid-β protein, and,
  selecting a the candidate compound that regulates the aggregation or deposition of amyloid-β protein;

[12] a method of screening for a compound that regulates expression of a protein encoded by a polynucleotide according to [1], wherein said method comprises the following steps of:
  (1) contacting a candidate compound with a cell, wherein a vector has been introduced into said cell, said vector comprising:
    an expression regulatory region of a gene comprising a nucleotide sequence selected from the group consisting of SEQ ID NO. 1, SEQ ID NO. 3, SEQ ID NO. 5, SEQ ID NO. 7, and SEQ ID NO. 9, and,
    a reporter gene operably linked downstream of the expression regulatory region,
  (2) measuring the activity of the reporter gene, and,
  (3) selecting the candidate compound that increases or decreases the reporter activity measured in step (b) when compared to the control;

[13] a pharmaceutical agent comprising a compound obtained by the method according to [11] or [12];

[14] a pharmaceutical agent comprising the peptide or protein according to [3] or [4];

[15] a pharmaceutical agent comprising an antisense polynucleotide complementary to the protein-coding sequence of a polynucleotide according to [1];

[16] the pharmaceutical agent according to [13] or [14], wherein said pharmaceutical agent is a preventive or therapeutic agent for Alzheimer's disease; and,

[17] a method for detecting Alzheimer's disease, comprising the following steps of:
 (1) measuring the expression of a polynucleotide according to [1];
 (2) comparing the measurement obtained by (1) with that obtained when the polynucleotide is expressed in healthy subjects; and,
 (3) linking Alzheimer's disease with said change in expression of the polynucleotide.

The proteins of the present invention that suppress or promote the aggregation of amyloid-β protein, and the polynucleotides encoding the proteins comprise the whole or part of the sequence shown in SEQ ID NO. 1, 3, 5, 7 or 9.

The polynucleotides of the present invention may include any nucleotide that can encode the proteins of the present invention, such as genomic DNA and chemically-synthesized DNA as well as cDNA, but are not limited thereto. The polynucleotides of the present invention may also include polynucleotides having any nucleotide sequence that is based on the degeneracy of the genetic code, as long as the polynucleotides encode the proteins of the present invention. The polynucleotides encoding the proteins of the present invention may be isolated by conventional methods, such as hybridization using as a probe a polynucleotide sequence shown in SEQ ID NO. 1, 3, 5, 7 or 9, or a partial sequence thereof, or PCR using primers designed based on the information of these sequences.

A protein of the present invention that suppresses or promotes amyloid-β protein aggregation, can be obtained by expressing the protein in a transformant using an expression vector comprising the open reading frame within the sequence shown in, for example, SEQ ID NO. 1, 3, 5, 7 or 9. These expressed proteins may be purified and isolated, using conventional methods, from the culture or cell fraction. Specifically, methods for purification and isolation are, for example, as follows: first, the cells or supernatant is collected using conventional methods, such as filtration and centrifugation, and the cell membranes and/or the cell walls are then treated by sonication and/or with lysozyme to obtain a cell membrane fraction. Subsequently, the cell membrane fraction thus obtained is dissolved in a suitable solution. From the supernatant or the cell membrane fraction, the protein of the invention is isolated and purified according to conventional methods generally used for purification and isolation of a natural or synthetic protein. Examples of methods for isolation or purification include dialysis, gel filtration, affinity chromatography using a monoclonal antibody against the proteins of the present invention or a partial peptide thereof, column chromatography using an appropriate absorbent, high performance liquid chromatography, etc.

Furthermore, the present invention includes polynucleotides encoding proteins functionally equivalent to the proteins described above. As used herein, the term "functionally equivalent" means that the protein of interest has an activity that suppresses or promotes amyloid-β protein aggregation. The activity that suppresses or promotes amyloid-β protein aggregation can be confirmed by using, for example, the methods described in the working examples. Aβ and its fragments are prone to aggregate under particular conditions. Addition of a test compound under such conditions would give rise to Aβ aggregates, if the test compound had a property that promotes aggregation. A fragment comprising the N-terminal amino acid sequence (residues 1–28) of Aβ has been used in experiments of this sort as a partial peptide having Aβ-aggregating activity (Methods in Enzymology Vol. 309, 274–284, 1999) Aβ aggregation can be detected optically, or can be confirmed microscopically after staining with Congo red and such.

One skilled in the art would be able to prepare proteins functionally equivalent to the proteins used in the β-amyloid aggregation tests described in the working examples below, for example, by using a method for introducing mutations into the amino acid sequences of proteins (e.g. site-directed mutagenesis, Current Protocols in Molecular Biology edit. Ausubel et al. (1987) Publish. John Wily & Sons Section 8.1–8.5) Such proteins might occur due to spontaneous mutation of amino acids in nature. The present invention also includes a protein having an amino acid sequence in which one or several amino acid residues are different from those found in a sequence of any one of the proteins identified in the working examples below (SEQ ID NO. 2, 4, 6, 8 or 10, or the amino acid sequence encoded by SEQ ID NO. 1, 3, 5, 7 or 9) due to a substitution, deletion, insertion and/or addition, as long as the protein retains a function equivalent to the proteins identified in the working examples below.

Number or sites of amino acid mutations in the protein are not limited, as long as the protein function is retained. The number (percentage) of mutations is typically 10% or less, preferably 5% or less, and more preferably 1% or less of the total amino acids. Alternatively, the mutation of "several" amino acids as used in the present invention includes the mutation of a "few" amino acids as well. "Few" refers to, for example, five, four, three, two, or one amino acid. Preferably, in view of maintaining protein function, substituting amino acids may have properties similar to the amino acids to be substituted. For example, Ala, Val, Leu, Ile, Pro, Met, Phe, and Trp are all classified into nonpolar amino acids, and they are thought to share common properties. Uncharged amino acids include Gly, Ser, Thr, Cys, Tyr, Asn, and Gln. Acidic amino acids include Asp and Glu, and basic amino acids include Lys, Arg, and His.

Alternatively, a protein functionally equivalent to the protein identified in the working examples below can be isolated using a hybridization or gene amplification technique well known to one skilled in the art. More specifically, using the hybridization technique (Current Protocols in Molecular Biology edit. Ausubel et al. (1987) Publish. John Wily & Sons Section 6.3–6.4), one skilled in the art would routinely be able to isolate a polynucleotide showing a significant homology to any one of the polynucleotide sequences encoding the proteins identified in the working examples below (SEQ ID NO. 1, 3, 5, 7 or 9) by using a polynucleotide sequences, or a portion thereof, and obtain a functionally equivalent protein from the polynucleotide isolated. The present invention includes a protein encoded by a polynucleotide hybridizing to a polynucleotide encoding a protein identified in the working examples below, as long as the proteins are functionally equivalent. A functionally equivalent protein can be isolated from animals including, but not limited to, vertebrates such as humans, mice, rats, rabbits, pigs, and cattle. From these animals, one can isolate genes that originated from molecular-evolutionarily the same gene that encodes a protein of the present invention that suppresses or promotes amyloid β protein aggregation. As used herein, the term "genes that originated from molecular-evolutionarily the same gene" refers to genes that are rationally judged to have evolved from one ancestor gene from which the human gene of the present invention evolved in the course of molecular-evolution. This judgment is based on polynucleotide sequence analysis of the genes or analysis of their physiological roles and such. Such genes maintain a significant nucleotide sequence homology among them.

Stringent hybridization conditions for isolating a polynucleotide encoding a functionally equivalent protein are, typical washing conditions such as "1×SSC, 0.1% SDS, 37° C.". More stringent conditions are, for example, "0.5×SSC, 0.1% SDS, 42° C.", and even more stringent conditions are, for example, "0.1×SSC, 0.1% SDS, 65° C.". The more stringent the hybridization conditions become, the more homologous to the probe sequence the polynucleotide is expected to be. Note that the above combinations of SSC, SDS, and temperature are given only for illustration, and one skilled in the art can achieve the same level of stringency by combining these factors appropriately to determine the hybridization conditions. The factors include those described above, or other factors (e.g. probe concentrations, length of probes, reaction time, etc.).

In general, a protein isolated using such hybridization techniques shows a significant homology in the nucleotide sequence encoding the protein, or in its amino acid sequence, compared to the sequence of a protein of the present invention, shown in SEQ ID NO. 2, 4, 6, 8 or 10, or a protein encoded by the a sequence shown in SEQ ID NO. 1, 3, 5, 7 or 9. "Significant homology" refers to a sequence identity of at least 60% or more, preferably 70% or more, more preferably 80% or more, even more preferably 90% or more, and most preferably 95% or more. Sequence homology can be determined using the BLAST 2 search algorithm (Altschul, S. F. et al, 1997, Gapped BLAST and PSI-BLAST: a new generation of protein database search programs, Nucleic Acids Res. 25: 3389–3402).

A gene-amplification technique (PCR) (Current protocols in Molecular Biology edit. Ausubel et al. (1987) Publish. John Wiley & Sons Section 6.1–6.4) can be used to design primers based on a part of any of the polynucleotide sequences identified in the working examples below (SEQ ID NO. 1, 3, 5, 7 or 9), and to isolate a polynucleotide fragment that shows a significant homology to the above polynucleotide sequence or a portion thereof, to obtain a protein functionally equivalent to the protein identified in the working examples.

The present invention also relates to a partial peptide of the proteins of the present invention and to a polynucleotide encoding the partial peptide. A partial peptide of the present invention comprises at least 7 amino acid residues, preferably 9 or more amino acid residues, more preferably 12 or more amino acid residues, even more preferably 15 or more amino acid residues. The partial peptide of the present invention may be produced by, for example, genetic engineering, a well-known technique for peptide synthesis, or cleavage of the proteins of the present invention with an appropriate peptidase.

The present invention also provides expression vectors comprising any one of the polynucleotides mentioned above. Furthermore, the present invention relates to transfectants harboring any of the expression vectors or polypeptides mentioned above, and a method for producing proteins or partial peptides thereof that suppress or promote amyloid-β protein aggregation. Such a method comprises culturing the transfectant and isolating a protein of the present invention from the culture. Moreover, the present invention provides the protein or partial peptide produced by the above method.

When producing polypeptides by means of genetic recombination, the type and extent of glycosylation of a polypeptide of interest would differ depending on the type of host cell. Furthermore, in the method of so-called "secretory production" of polypeptides, it is well known to one skilled in the art that (N- and/or C-) terminal amino acid sequences of precursor peptides expressed in host cells would undergo processing by signal peptidases and such to produce polypeptides having various terminal sequences. Therefore, one skilled in the art would easily understand that such polypeptides are also included in the proteins of the present invention.

The working examples described below illustrates only an example of constructing a vector that functions in mammalian cells as an expression vector. However, since the polynucleotide sequences encoding the proteins of the present invention are disclosed herein, it would be easy for one skilled in the art to construct an expression vector that can express and produce a protein of the present invention when such a vector is introduced into a fungal host cell, such as a yeast, or a prokaryotichost cell. Therefore, the present invention includes expression vectors constructed using any methods known in the art based on the polynucleotide sequences of the present invention.

Microbial cells that can be used for the expression of the polynucleotides encoding the proteins of the present inventions include, for example, prokaryotic bacteria (e.g. *Escherichia coli* and *Bacillus subtilis*) and eukaryotic yeasts (e.g. *Saccharomyces cerevisiae*). Mammalian cells include cultured human cells and cultured animal cells. Moreover, cultured plant cells can be used.

Examples of microorganisms include bacteria of the genus *Escherichia* (e.g. *E. coli* HB101 ATCC 33694, *E. coli* HB101-16 FERM BP-1872, *E. coli* MM294 ATCC 31446, *E. coli* DH1 ATCC 33849, etc.) and baker's yeast (e.g. *S. cerevisiae* AH22 ATCC 38626, etc.). Examples of mammalian cells include HEK293 cells derived from human embryonic kidney cells, mouse L929 cells, Chinese hamster ovary (CHO) cells, etc.

Generally, expression vectors are constructed with, at least, a promoter, an initiation codon, a polynucleotide encoding the amino acid sequence of any of the proteins of the present invention, a termination codon, and a self-replication unit, when prokaryotes, bacteria, particularly *E. coli* are used as host cells. When eukaryotic cells such as yeast and mammalian cells are used, expression vectors are preferably constructed with, at least, a promoter, an initiation codon, a polynucleotide encoding the amino acid sequence of any of the proteins of the present invention, and a termination codon. Additionally, an enhancer sequence, 5'- and 3'-untranslated regions for the proteins of the present invention, a polyadenylation site, and a self-replication unit may be integrated.

The self-replication unit preferably comprises a selectable marker for transfectants (e.g. resistance to ampicillin). In the case of expression vectors using bacteria as host cells, the term "promoter" means a promoter-operator region containing a promoter, operator, and a Shine-Dalgarno (SD) sequence (e.g. AAGG, etc.). Examples of such promoters include conventional promoter-operator regions (e.g. the lactose operon, PL-promoter, trp-promoter, etc.). An Example of a promoter for expression vectors used in yeast host cells includes the pho5 promoter. Additionally, to facilitate purification, basic amino acids having affinity for chelated metal ions can be added to either end of a protein of the present invention.

When basic amino acids are added, a primer having, at its 5'-end, a nucleotide sequence sequentially coding for desired amino acid residues can be used for PCR to introduce an oligonucleotide at either end of a gene of interest. Histidine, lysine, arginine, and such can be used as basic amino acids.

Examples of promoters used in expression vectors in mammalian cells include the HTLV-LTR promoter, early and late SV40 promoters, CMV promoters, the mouse metallothionein I (MMT) promoter, etc. A preferred example of an initiation codon is the methionine codon (ATG).

A polynucleotide encoding an amino acid sequence of the proteins of the present invention may be obtained by, for example, partial or complete synthesis of nucleotides using a DNA synthesizer. Alternatively, it can be obtained from a human cDNA library by using a probe or primer set that is designed based on a nucleotide sequence as shown in SEQ ID NO. 1, 3, 5, 7 or 9. The genomic DNA encoding the proteins of the present invention can also be prepared by treating genomic DNA according to a conventional method (e.g. digestion with restriction enzymes, dephosphorylation by bacterial alkaline phosphatase, phosphorylation by T4 polynucleotide kinase, and ligation with T4 DNA ligase). Furthermore, the genomic DNA thus obtained can be used to demonstrate the transcriptional initiation site of a gene of the present invention located on the genome. This allows one to specify expression-regulatory regions located upstream of the gene. Regulatory regions, such as promoters and enhancers, which would control expression of the a encoding a protein of the present invention, are useful as target regions for detecting aberrant expression of a protein of the present invention. Regulation of gene expression can be achieved using decoy nucleotide pharmaceuticals that target such regions.

The host cells of the present invention include cells used for functional analysis of the proteins of the present invention and those used for screening inhibitors or enhancers of the functions of the proteins. Introduction of a vector into host cells may be conducted using any of the methods including, for example, calcium phosphate precipitation, electroporation (Current protocols in Molecular Biology edit. Ausubel et al. (1987) Publish. John Wiley & Sons. Section 9.1–9.9), the lipofectamine method, and microinjection. Preparation of the proteins of the present invention from transfectants may be conducted using any of the isolation and purification methods well known to one skilled in the art.

The present invention also provides a polynucleotide comprising at least 15 nucleotides, which is complementary to any of the polynucleotide sequences shown in SEQ ID NO. 1, 3, 5, 7, or 9, or to a complementary strand thereof. As used herein, the term "complementary strand" refers to one strand of a double-stranded polynucleotide that forms base pairs of A:T (A:U) and G:C with the other strand of the polynucleotide. Also, "complementary" is defined as not only sequences that completely match a continuous nucleotide region of at least 15 nucleotides, but also sequences having a homology of at least 70%, preferably 80% or more, more preferably 90% or more, and most preferably 95% or more to that region. Sequence homology can be determined according to the algorithm as described in this description.

Such a polynucleotide can be used as a probe for isolating and detecting the DNA or RNA encoding a protein of the invention, or as a primer for amplifying a polynucleotide. When used as a primer, the DNA usually comprises 15–100 bp, and preferably, 15–35 bp. When used as a probe, the DNA comprises the entire sequence of a DNA of the invention, or at least a part of it, and comprises at least 15 bp. When used as a primer, the 3'-region of the polynucletide must be complementary, but the 5'-terminal may contain additional sequences, such as a restriction enzyme recognition site or a tag.

The polynucleotides of the present invention can be used for testing or diagnosing aberrations in the proteins of the present invention. For example, the polynucleotides of the present invention can be used as probes or primers to test aberrations in gene expression by Northern hybridization or RT-PCR. As used herein, the term "expression" includes transcription and/or translation. Expression analysis of the polynucleotides of the present invention may allow the testing and diagnosing of gene expression at the transcriptional level. Gene expression at the translational level may be tested or diagnosed by using antibodies raised against the proteins of the present invention as described below. Polymerase chain reaction (PCR) using as a primer a polynucleotide of the present invention, such as genomic DNA-PCR and RT-PCR, can amplify a polynucleotide encoding a protein of the present invention or an expression regulatory region. Sequence aberrations can be tested or diagnosed using RFLP analysis, SSCP, sequencing, and such.

Moreover, "a polynucleotide comprising at least 15 nucleotides, which is complementary to any of the polynucleotide sequences as set forth in SEQ ID NO. 1, 3, 5, 7 and 9, or to a complementary strand thereof" include antisense polynucleotides for inhibiting the expression of the proteins of the present invention. Antisense polynucleotides comprise at least 15 bp or more, preferably 100 bp or more, more preferably 500 bp or more, and usually 3000 bp or less, preferably 2000 bp or less.

Such antisense polynucleotides are expected to be applied in gene therapy for diseases caused by aberrations (in function or expression) in the proteins of the present invention. Specifically, in Alzheimer's disease, the aggregation and deposition of amyloid-β protein trigger the disease and lead to the cell death of cranial nerve cells and neural dysfunctions. Therefore, if the expression of a protein of the present invention that promotes amyloid-β protein aggregation can be inhibited, it may be useful in the treatment or prevention of Alzheimer's disease. In addition, an Alzheimer's disease model system can be produced if the expression of a protein of the present invention that suppresses amyloid-β protein aggregation can be inhibited, which will result in the promotion of amyloid-β protein aggregation. An antisense polynucleotide can be prepared, for example, by utilizing the phosphorothioate method based on the sequence information of a polynucleotide sequence shown in SEQ ID NO. 1, 3, 5, 7 or 9 ("Physicochemical properties of phosphorothioate oligodeoxynucleotides." Stein (1988) Nucleic Acids Res. 16: 3209–3221).

A polynucleotide or antisense polynucleotide of the present invention can be used in gene therapy, for example, by administrating it to a patient by utilizing the in vivo or ex vivo method using vectors such as retrovirus vectors, adenovirus vectors, and adeno-associating virus vectors, or non-virus vectors such as liposomes.

The present invention also relates to an antibody capable of binding to a protein of the invention. The form of the antibody is not especially restricted; it includes polyclonal antibodies, monoclonal antibodies, or portions thereof, which are capable of binding to an antigen. It also includes antibodies of all classes. Furthermore, specialized antibodies such as humanized antibodies are also included.

If the antibody is a polyclonal antibody, it can be obtained according to the standard method by synthesizing a protein of this invention, or a partial peptide thereof, and immunizing rabbits with the protein or peptide (Current Protocols in Molecular Biology (1987) Ausubel et al. edit, John Wily & Sons, Section 11.12–11.13). If the antibody is a monoclonal antibody, it can be obtained by immunizing mice with a protein of this invention, or a partial peptide thereof, and producing a hybridoma cell by fusing spleen cells and myeloma cells (Current Protocols in Molecular Biology (1987) Ausubel et al. edit, John Wily & Sons, Section 11.4–11.11).

An antibody capable of binding to a protein of the present invention can be used for purifying a protein of the invention, and also for detecting and/or diagnosing aberrations in the expression and the structure of the protein. Specifically, proteins may be extracted from tissues, blood, or cells, and methods such as western blotting, immunoprecipitation, or ELISA can be used for the above purpose.

Furthermore, an antibody capable of binding to the proteins of the present invention may be utilized for treating diseases associated with the protein. If the antibody is used for treating patients, a human antibody or humanized antibody is desirable in terms of their low antigenicity. Human antibodies can be prepared by immunizing a mouse in which the immune system has been replaced with that of a human ("Functional transplant of megabase human immunoglobulin loci recapitulates human antibody response in mice" Mendez M. J. et al. (1997) Nat. Genet. 15: 146–156, for a reference). Humanized antibodies can be prepared by recombination of the hyper variable region of a monoclonal antibody (Methods in Enzymology (1991) 203: 99–121).

Among the proteins of the present invention, the proteins encoded by the polynucleotides of SEQ ID NOs. 1, 3 and 7 have an inhibitory activity on amyloid-β protein aggregation, and as shown in the Examples below, their expression decreases in patients with Alzheimer's disease. Therefore, augmentation of the expression level of these proteins will prevent amyloid-β protein aggregation, and will be useful for the treatment and prevention of Alzheimer's disease. Additionally, these proteins, and their functional equivalents, can themselves be used as therapeutic and preventive agents for Alzheimer's disease.

Among the proteins of the present invention, the proteins encoded by the polynucleotides of SEQ ID NOs. 5 and 9 have an enhancing activity on amyloid-β protein aggregation, as shown in the working examples below, and their expression increases in patients with Alzheimer's disease. Therefore, reduction of the expression level of these proteins will prevent amyloid-β protein aggregation, and will be useful for the treatment and prevention of Alzheimer's disease.

Moreover, the proteins of the present invention are expected to relate to other amyloidoses, specifically, schizophrenia and related neuropathies, rheumatoid arthritis, tuberculosis, leprosy, bronchitis, systemic lupus erythematosus (SLE), dialysis amyloidosis, diabetic amyloidosis, atrial amyloidosis, and such, and they can be used as therapeutic and preventive agents for these diseases, or for screening such therapeutic and preventive agents.

The present invention provides a method of screening for compounds regulating the activity of the proteins of the present invention. Since the proteins of the present invention prevent or promote amyloid-β protein aggregation, such compounds may be useful as therapeutic and preventive agents for Alzheimer's disease by regulating the expression of the gene products. This screening is conducted as follows.

A candidate compound that can prevent amyloid-β protein aggregation may be selected by contacting the candidate compound with a protein of the present invention, or cells expressing the protein, under conditions that permit amyloid-β protein aggregation.

More specifically, any of the proteins of the present invention, for example, a protein encoded by the nucleotide sequence of SEQ ID NO. 1, 3, 5, 7 or 9, or a protein functionally equivalent to the protein, or a cell expressing the protein, is incubated with a candidate compound in a solution containing amyloid-β protein (Aβ40, Aβ42, Aβ28, etc.). Subsequently, to determine the degree of aggregation, fluorescence intensity is measured using a fluorescent dye such as thioflavin-T, which binds to, for example, aggregated amyloid-β protein.

Among the proteins of the present invention, the increase of the expression of a protein encoded by a polynucleotide as set forth in SEQ ID NOs. 1, 3 or 7 would inhibit amyloid-β protein aggregation and thus be useful for the treatment and prevention of Alzheimer's disease. A reduction of the expression of a protein encoded by a polynucleotide as set froth in SEQ ID NOs. 5 or 9 would prevent amyloid-β protein aggregation, and thus is useful for the treatment and prevention of Alzheimer's disease. Therefore, compounds that can regulate the expression of the genes encoding the proteins of the present invention are useful as therapeutic and preventive agents. Thus, the present invention relates to a method of screening for a compound that can regulate the expression of a protein encoded by a polynucleotide of the present invention, which method comprises the following steps of:

(1) contacting a candidate compound with a cell, wherein a vector has been introduced into said cell, said vector comprising:
    an expression regulatory region of a gene comprising a nucleotide sequence selected from the group consisting of SEQ ID NO. 1, and,
    a reporter gene operably linked downstream of the expression regulatory region,
(2) measuring the activity of the reporter gene, and,
(3) selecting the candidate compound that increases or decreases the reporter activity measured in step (2) when compared to the control.

To carry out the screening method of the present invention, a regulatory region of the gene is isolated from chromosomal DNA, and an expression plasmid is prepared in which a reporter gene (e.g. luciferase, β-galactosidase, GFP (green fluorescent protein), etc.) is linked downstream of the regulatory region. A regulatory region that controls expression of a gene comprising a nucleotide sequence selected from the group consisting of SEQ ID NO. 1, SEQ ID NO. 3, SEQ ID NO. 5, SEQ ID NO. 7, and SEQ ID NO. 9 may be cloned from chromosomal DNA by any method well known in the art. For example, S1 mapping is well known as a method for specifying transcription initiation sites ("Isolation of Transcriptional Regulatory Region" and "Isolation and Purification of Transcription Factors" in Department Oncology, The Institute of Medical Science (ed.), "Current Protocols for Cellular Engineering", Cell Technology, Separate Volume 8, pp. 362–374, Shujunsha Co. Ltd., 1993). In general, screening of a human genomic library using a 15–100 bp, preferably 30–50 bp fragment at the 5' terminus of the gene may allow cloning of the DNA for the regulatory region controlling gene expression as a cloned gene comprising the expression regulatory region. The cloned DNA thus obtained often contains 10 kb or longer sequence of the 5'-untranslated region of the gene. Then, the 5'-terminal region of the cloned DNA is shortened or fragmented by treating with, for example, an exonuclease. The minimal unit essential for maintaining the activity of the regulatory region can be found by evaluating the expression level or regulation of expression of the reporter gene using a sequence comprising a shortened expression regulatory region (deletion study). A computer program that predicts expression-regulatory regions of genes using Neural Network is widely known (http://www.fruitfly.org/seq_tools/promoter.html, Reese, M. G., et al, "Large Scale Sequencing Specific Neural Networks for Promoter and Splice Site Recognition" Biocomputing: Proceedings of the 1996 Pacific Symposium, edited by Lawrence Hunter and Terri E. Klein, World Scientific Publishing Co, Singapore, Jan. 2–7, 1996). Alternatively, the minimal unit essential for maintaining the activity is predicted using a program such as the Promoter Scan program that searches for a transcription factor binding sequence and predicts the expression regulatory region (http://biosci.cbs.umn.edu/software/proscan/promoterscan.htm, Prestridge, D. S. 1995, Prediction of Pol II Promoter Sequence using Transcription Factor Binding Sites. J. Mol. Biol. 249: 923–932). The deletion study can be conducted, focusing on the core regions predicted.

An expression plasmid in which a reporter gene is operably linked downstream of the thus isolated gene for the regulatory region is constructed and introduced into an appropriate cell. As used herein, the term "operably linked" means that the two elements are linked so that transcription of the reporter gene is initiated by activation of the above expression regulatory region. Any gene may be used as a reporter gene as long as it encodes a protein that allows one to observe an activation of the above regulatory region as an expression of the gene. Particularly, genes such as luciferase, β-galactosidase, GFP (Green Fluorescent Protein) are typically used as reporter genes. Mammalian cells having a deletion in the corresponding gene, for example, can be used as cells for introducing the vector. Next, mammalian cells having a deletion in the corresponding gene, for example, are transfected with the expression plasmid. Expression of the reporter gene resulting from transcriptional activation by the regulatory region may be detected as a color development, luminescence, and so on. Under these conditions, this cell strain is seeded into a 96-well multiplate and compounds to be screened are added to each well, thereby allowing easy selection of compounds that can prevent or promote the expression of gene products. As a method for selecting a compound, if GFP is used as the reporter gene, the fluorescence intensities between the presence and absence of the compound can be compared. Comparison refers to when the luminescence ration is two-folds or higher, or 1/2 or lower, preferably five-folds or higher, or 1/5 or lower, and more preferably 10-folds or higher, or 1/10 or lower. This method can be applied to not only animal cells, but also other cells, regardless of being of eukaryotic or prokaryotic origin, as long as they can express a reporter gene in a similar system.

Test samples used in the screening include, for example, cell extracts, expression products of a gene library, synthetic low molecular weight compounds, synthetic peptides, naturally occurring compounds, etc. Note that these test compounds are examples and the present invention is not limited thereto.

Compounds isolated by this screening are candidates for a compound that promotes or suppresses the activity of a protein of the present invention (agonist or antagonist). They are also candidates as compounds that inhibit the interaction between the proteins of the present invention and certain molecules that interact with the proteins. These compounds may be possibly applied to the treatment or prevention of diseases related to the proteins of the present invention.

Further, the present invention relates to use of the compounds obtainable by the screening of the present invention for medical purposes. Thus, the present invention relates to the use of an agent comprising a compound obtainable by the aforementioned screening method as a main ingredient, in the treatment and prevention of Alzheimer's disease, or in the regulation of amyloid β protein aggregation. The present invention also relates to a therapeutic and preventive agent comprising such a compound as a main ingredient. Furthermore, compounds obtained by the screening method of the present invention are expected to be related to other amyloidoses, specifically, schizophrenia and related neuropathies, rheumatoid arthritis, tuberculosis, leprosy, bronchitis, SLE, dialysis amyloidosis, diabetic amyloidosis, atrial amyloidosis, etc., and can be used as therapeutic and preventive agents for these diseases and for screening such therapeutic and preventive agents.

The proteins, nucleotides, antibodies of the present invention and the compounds isolated by the above screening mentioned are useful for regulating amyloid β protein aggregation. When used as pharmaceutical agents, they themselves can be used as pharmaceutical agents, or they can be formulated for use by any known pharmaceutical method. For example, the compounds can be formulated by mixing with pharmacologically acceptable carriers or vehicles, specifically, sterilized water, physiological saline, plant-oil, emulsifiers, suspending agents, and used. Methods well known to one skilled in the art may be used to administer a pharmaceutical agent to patients, for example as intra-arterial, intravenous, percutaneous injections, and so on. The dosage varies according to the body-weight and age of the patient, and also the administration method, but one skilled in the art can suitably select an appropriate dosage. If the compound can be encoded by a polynucleotide, the polynucleotide can be inserted into a vector for gene therapy to perform the therapy. The dosage and method of administration vary according to the body-weight, age, and symptoms of a patient, but one skilled in the art can select them suitably.

The proteins of the present invention are predicted to have other physiological activities, in addition to the activity of suppressing or promoting amyloid β protein aggregation. Such activities can be determined as follows: Since the proteins of the present invention are secretory or membrane proteins, and their amino acid sequences have been elucidated, it is possible to analyze whether they have other physiological activities, in addition to the activity of suppressing or promoting amyloid β protein aggregation, by expressing recombinants in appropriate expression systems, or by using antibodies that specifically recognize the proteins.

The biological activities of each protein of the present invention can be analyzed, based on, for example, "Glycobiology" M. Fukuda and A. Kobata (ed.), 1993; "Growth Factors" I. McKay and I. Leigh (ed.), 1993; and "Extracellular Matrix" M. A. Haralson and J. R. Hassell (ed.), 1995; in "The Practical Approach Series", IRL PRESS, or "Glycoprotein Analysis in Biomedicine" Elizabeth F. Hounsell (ed.), 1993; in "Method in Molecular Biology" series, Humana Press. Alternatively, biological activities related to secretory or membrane proteins can be analyzed based on the disclosures found in "Growth and differentiation factors and their receptors", The Japanese Biochemical Society (ed.), Shin-Seikagaku Jikken Kouza Vol. 7 Tokyo-Kagaku-Doujin Co. Ltd, 1991, and in Volume 296 "Neurotransmitter Transporters"; Volume 294 "Ion Channels (Part C)"; Volume 293 "Ion Channels (Part B)", Volume 292 "ABC Transporters"; Volume 288 "Chemokine Receptors"; Volume 287 "Chemokines"; Volume 248 "Proteolytic Enzymes"; Volume 245 "Extracellular Matrix Components"; Volume 244 "Proteolytic Enzymes"; Volume 230 "Guide to Techniques in Glycobiology"; Volume 198 "Peptide Growth Factors"; Volume 192 "Biomembranes"; Volume 191 "Biomembranes"; Volume 149 "Drug and Enzyme Targeting", in "Methods in Enzymology", Academic Press, and so on.

A pharmaceutical agent can be made based on functional analyses using a secretory or membrane protein.

In the case of a membrane protein, it would most likely be a protein having a function as a receptor or ligand by being expressed on the cell surface. Therefore, it is possible to reveal a new ligand-receptor relationship by screening a membrane protein of the invention based on the binding activity with a known ligand or receptor. Screening can be performed according to known methods.

For example, a screening using cells expressing a receptor proteins of the present invention can be performed as follows. Namely, it is possible to screen a receptor capable of binding to a specific protein by using the following steps of: (a) contacting a cell sample with a protein of the invention, or a partial peptide thereof, and (b) selecting a cell that binds to the protein or peptide.

This screening can be conducted, for example, as follows. First, a protein of the invention is expressed, and the recombinant protein is purified. Next, the purified protein is labeled, binding assay is performed using various cell lines or primary cultured cells, and cells that are expressing a receptor are selected (Growth and differentiation factors and their receptors, Shin-Seikagaku Jikken Kouza Vol. 7 (1991) Honjyo, Arai, Taniguchi, and Muramatsu edit, p203–236, Tokyo-Kagaku-Doujin). Protein labeling can be achieved by labeling with radioisotopes (RI) such as $^{125}$I, and by enzymes (alkaline phosphatase etc.) as well Alternatively, a protein of the invention may be used without labeling, and then detected by using a labeled antibody against the protein. The cells that are selected by the above screening methods, which express a receptor of a protein of the invention, can be used for further screening agonists or antagonists of the receptor.

Once a receptor of a protein of the invention or the cells expressing the receptor is obtained by screening, it is possible to screen a compound that inhibits the binding between the protein and its receptor (agonists or antagonists of the receptor, for example) by utilizing the binding ability of the protein to its receptor or cells expressing the receptor.

The screening method comprises the steps of: (a) contacting a protein of the invention with its receptor or cells expressing the receptor in the presence of a test sample, (b) detecting the binding activity between the protein and its receptor or the cells expressing the receptor, and (c) selecting a compound that can reduce the binding activity compared to the activity in the absence of the sample.

Test samples that can be used in the screening include cell extracts, expression products of a gene library, synthesized low molecular compounds, synthesized peptides, and natural compounds, for example, but are not limited thereto. A compound that is isolated by the above screening using the binding ability of a protein of the invention can be also used as the test sample.

A compound isolated by the screening may be a candidate for an agonist or an antagonist of a receptor of a protein of the invention. By utilizing an assay that monitors a change in intracellular signaling such as phosphorylation, which results from the reduction of the binding between the protein and its receptor, it is possible to identify whether the obtained compound is an agonist or antagonist of the receptor. Also, the compound may be a candidate for a molecule that can inhibit the interaction between a protein of the invention and its associating proteins (including receptors) Such compounds can be used for developing drugs for preventing or treating a disease associated with the protein of the invention.

When a protein of the invention is a secretory protein, it may be a factor that can regulate cellular conditions such as growth and differentiation. A novel factor that regulates cellular conditions can be discovered by adding the secretory protein of the invention to a certain kind of cell, and performing screening by utilizing a cellular change in growth or differentiation, or activation of a particular gene.

The screening may be performed, for example, as follows. First, the protein of the invention is expressed and the recombinant protein is purified. Then, the purified protein is added to various kinds of cell lines or primary cultures, and a change in the cell growth and/or differentiation is monitored. Alternatively, the induction of a particular gene that is known to be involved in a certain cellular change can be detected at the level of mRNA expression or protein amount. Alternatively, the amount of an intracellular molecule (low molecular compounds) that is changed by the function of a gene product (protein) that is known to be functioning in a certain cellular change may be used for the detection.

Once the screening reveals that a protein of the invention can regulate cellular conditions or functions, it is possible to apply the protein as a pharmaceutical agent for related diseases by itself or by altering a part of it.

As was described for membrane proteins, secretory proteins provided by the invention may be used to explore a novel ligand-receptor interaction using a screening based on the binding ability to a known ligand or receptor. A similar method can be used to identify an agonist or antagonist. The resulting compounds obtained by the methods can be candidates for compounds that can inhibit the interaction between a protein of the invention and an interacting molecule (including receptors). Such compounds may used as pharmaceutical agents for preventing and treating diseases, in which the protein may play a certain role.

If a protein or gene that is affected by the screening turns out to be associated with a disease, it is possible to screen a gene or compound that can regulate its expression and/or activity either directly or indirectly by utilizing a protein of the present invention.

For example, a protein of the invention is expressed and purified as a recombinant protein. Then, the protein or gene that is affected by the screening is purified, and screened by the binding ability. Alternatively, the screening can be performed by adding in advance a compound that is a candidate for an inhibitor, and observing changes in binding. Compounds obtained by such a screening can be used for developing pharmaceutical agents for diseases with which a proteins of the present invention is associated. Similarly, if a regulatory factor obtained by the screening turns out to be a protein, a compound that affects the original expression level and/or activity of the protein can be used for the same purpose described above.

If a secretory or membrane proteins of the present invention has an enzymatic activity, it is possible to identify the activity by adding a compound to the protein under appropriate conditions, and monitoring a change of the compound. It is also possible to screen a compound that inhibits an activity of a protein of the invention by utilizing the activity as an index.

In a screening given as an example, a protein of the invention is expressed and the recombinant protein is purified. Then, a compound is added to the purified protein, and the amount of the compound and the reaction products are examined. Alternatively, a compound that is a candidate for an inhibitor is pretreated, then the compound (substrate) that can react with the purified protein is added, and the amount of the substrate and the reaction products are examined.

The compounds obtained in the screening may be used as pharmaceutical agents for diseases with which a protein of the invention is associated.

Whether or not the secretory or membrane proteins of the present invention is a novel protein associated with a disease is determined using also methods other than those described above. Namely, this can be done by obtaining a specific antibody against a protein of the invention, and examining the relationship between the expression or activity of the protein and a certain disease. In an alternative way, it may be analyzed referring to methods in "Molecular Diagnosis of Genetic Diseases" (Elles R. edit, (1996) in the series of "Method in Molecular Biology" (Humana Press).

In addition to purifying a protein of the invention, an antibody that binds to a protein of the invention may be used, for example, for testing or diagnosing structural or functional aberrations of the protein of the present invention.

Polynucleotides of the present invention were observed to be aberrantly expressed in the hippocampus of patients with Alzheimer's disease. Therefore, Alzheimer's disease may be detected by measuring the expression of a polynucleotide of the present invention. Thus, the present invention relates to a method for detecting Alzheimer's disease, comprising the following steps of:

(1) measuring the expression of at least one of the polynucleotides selected from the group consisting of SEQ ID NO. 1, SEQ ID NO. 3, SEQ ID NO. 3, SEQ ID NO. 7, and SEQ ID NO. 9, (2) comparing the measurement obtained with that obtained when the polynucleotide is expressed in healthy subjects; and, (3) linking Alzheimer's disease with said change in expression of the polynucleotide.

In the present invention, an expression state of a polynucleotide can be understood by analyzing any one of the steps in the transcription of the gene into mRNA and in the translation into the protein. More specifically, the state of transcription can be understood by measuring mRNA comprising an aforementioned nucleotide sequence in place of an aforementioned polynucleotide. Any known method, such as Northern hybridization and RT-PCR, can be used to measure mRNA. Alternatively, measurement of a protein having an amino acid sequence encoded by a polynucleotide, or a fragment of the protein, would elucidate the state of translation into the protein. Proteins can be measured by Western blot using antibodies recognizing the proteins and various immunoassays. The testing method of the present invention can be conducted for blood samples and spinal fluid samples, or hippocampal tissue obtained by an autopsy. To observe the state of expression of the polynucleotides of the present invention, using tissue specimens as samples, analytical methods, such as in situ hybridization and immunohistological techniques, may be used if the state of expression of a polynucleotide of the present invention is analyzed, and if, for example, the expression of PSEC256 is found to be enhanced in the brain of AD patients compared to the expression in normal brains, PSEC256 can be linked to Alzheimer's disease. Also, if inhibition of the expression of PSEC0012, PSEC0220, PSEC0242, or such, is observed, they can also be linked to Alzheimer's disease.

The present invention also relates to a reagent for revealing an expression state of a polynucleotide of the present invention. More specifically, the present invention relates to the use of a polynucleotide comprising at least 15 nucleotides, which is complementary to any one of the polynucleotides of the present invention, or to a complementary strand thereof, for detecting a polynucleotide of the present invention. Alternatively, the present invention relates to the use of an antibody recognizing any one of the proteins of the present invention for detecting the protein.

BEST MODE FOR IMPLEMENTING THE INVENTION

The present invention shall be described in detail below with reference to examples, but it is not be construed as being limited thereto.

EXAMPLE 1

Cloning of cDNAs that Encode the Proteins Promoting or Preventing Aggregation and Deposition of Amyloid β Protein NT-2 neuron progenitor cells (Stratagene), a teratocarcinoma cell line from human embryo testis, which can differentiate into neurons when treated with retinoic acid, were used. The NT-2 cells were cultured according to the manufacturer's instructions, (1) without retinoic acid treatment (NT2RM1), (2) 2 weeks after retinoic acid was added to cultured NT-2 cells (NT2RP3)

The cells were harvested separately, from which mRNA was extracted by the method described in the literature (Molecular Cloning 2nd edition. Sambrook J., Fritsch, E. F., and Maniatis T. (1989) Cold Spring Harbor Laboratory Press). Poly (A) $^+$RNA was further purified from the mRNA using oligo-dT cellulose.

Similarly, human placenta (PLACE1), and brain-enriched tissues from human embryo (HEMBA1) were used to extract mRNA by the method described in the literature (Molecular Cloning 2nd edition. Sambrook J., Fritsch, E. F., and Maniatis T. (1989) ColdSpring Harbor Laboratory Press). Poly(A) $^+$RNA was further purified from the mRNA using oligo-dT cellulose.

Each poly(A) $^+$RNA was used to construct a cDNA library by the oligo-capping method (Maruyama M. and Sugano S. (1994) Gene 138: 171–174). Using the Oligo-cap linker (agcaucgagu cggccuuguu ggccuacugg/SEQ ID NO: 11) and the Oligo-dT primer (gcggctgaag acggcctatg tggcctttt tttttttttt tt/SEQ ID NO: 12), BAP (Bacterial Alkaline Phosphatase) treatment, TAP (Tobacco Acid Phosphatase) treatment, RNA ligation, the first strand cDNA synthesis, and removal of RNA were performed as described in the reference (Suzuki and Kanno (1996) Protein Nucleic acid and Enzyme. 41: 197–201; Suzuki Y. et al. (1997) Gene 200: 149–156). Next, 5'- and 3'-PCR primers ((agcatcgagt cggccttgtt g/SEQ ID NO: 13) and (gcggctgaag acggcctatg t/SEQ ID NO: 14) respectively) were used to perform PCR (polymerase chain reaction) to convert the cDNA into double stranded cDNA, which was then digested with SfiI. Then, the DraIII-cut pUC19FL3 vector (for NT2RM1), or pME18SFL3 (GenBank AB009864, expression vector; for NT2RP3, PLACE1, and REMBA1) was used for cloning the cDNA in an unidirectional manner, and cDNA libraries were obtained. The clones having an insert cDNA of 1 kb length or shorter were removed for NT2RM1, PLACE1, and HEMBA1, and the clones having an insert of 2 kb or shorter were removed for NT2RP3. Then, the nucleotide sequence of the 5'- and 3'-ends of the cDNA clones was analyzed using DNA sequencing reagents (Dye Terminator Cycle Sequencing FS Ready Reaction Kit, drhodamine Terminator Cycle Sequencing FS Ready Reaction Kit, or BigDye Terminator Cycle Sequencing FS Ready Reaction Kit, from by PE Biosystems), performing sequencing reactions according to the instructions, and analyzing with a DNA sequencer (ABI PRISM 377, PE Biosystems).

The pME18SFL3 eukaryotic expression vector was used for the construction of the cDNA libraries, except for NT2RM1. The vector contains SRα promoter and SV40 small t intron in the upstream of the cloning site, and SV40 polyA added signal sequence site in the downstream. As the cloning site has asymmetrical DraIII sites, and cDNA fragments contain a complementary SfiI site on their ends, the cloned cDNA fragments can be inserted downstream of the SRα promoter unidirectionally. Therefore, the plasmid clones containing full-length cDNA can be introduced directly into COS cells to be expressed transiently. Thus, experimental analysis as proteins (gene products) or as biological activities can be very easily carried out.

The fullness ratio of the 5'-end sequence of the cDNA clones in the libraries constructed by the oligo-capping method was determined as follows. For all the clones in which the 5'-end sequence was identical to that of any known human mRNA in the public database, the clones were judged to be "complete/full length", if they had a longer 5'-end sequences than the known human mRNA, or, even if the 5'-end sequence was shorter, if they contained a translation initiation codon. A clone that did not contain a translation initiation codon was judged to be "incomplete/not full length". The fullness ratio ((the number of complete clones)/(the number of complete clones)+(the number of incomplete clones)) of the 5'-end of the cDNA clones from each library was determined by comparing with the known human mRNA (NT2RM1: 69%; NT2RP3: 61%; PLACE1: 68%; REMBA1: 53%). The result indicates that the fullness ratio of the 5'-end sequence was extremely high.

The relationship between the cDNA libraries and the clones is shown below.

| HEMBA1: | PSEC0220 |
|---------|----------|
| NT2RM1: | PSEC0012 |
| NT2RP3: | PSEC0242, PSEC0256 |
| PLACE1: | PSEC0129 |

Furthermore the complete cDNA sequence and the predicted amino acid sequence of the clones thus selected were determined. The final nucleotide sequences were determined by combining the following three methods, and overlapping the nucleotide sequences determined by each method.

(1) Long read sequencing from both ends of the cDNA inserts using a Licor DNA sequencer (Sequence reactions were performed according to the manual of the Licor sequencer (Aloka), and DNA sequence was determined using the sequencer.)

(2) Nested sequencing by the Primer Island method which utilizes the in vitro integration reaction of AT2 transposon (Devine S. E., and Boeke J. D. (1994) Nucleic Acids Res. 22: 3765–3772) (Clones were obtained using a kit from PE Biosystems, and sequence reactions were performed using the DNA sequencing reagents from the same company, according to the manufacturer's instructions, and DNA sequence was determined using an ABI PRISM 377 sequencer).

(3) Primer walking by the dideoxy terminator method using custom synthesized DNA primers (Sequencing reactions were performed using the DNA sequencing reagents from PE Biosystems and custom synthesized DNA primers according to the manufacturer's instructions. DNA sequence was determined using an ABI PRISM 377 sequencer).

Obtained sequences were subjected to analysis by ATGpr [A. A. Salamov, T. NISHIKAWA, M. B. Swindells, Bioinformatics, 14: 384–390 (1998); http://www.hri.co.jp/atgpr/] and PSORT, and also to BLAST search of GenBank and SwissProt. As a result, most clones were predicted to be secretory or membrane proteins that contain a signal sequence at the N-terminus. For PSEC0242 and PSEC0256, no signal sequence was detected, but the presence of a transmembrane helix was identified by SOSUI, predicting that they are membrane proteins. The results of the above analyses suggest that PSEC0012, PSEC0129, and PSEC0220 are secretory or membrane proteins and have signal sequences at their N-termini, which indicates that they are full-length cDNA clones. PSEC0242 and PSEC0256are membrane proteins and are predicted to be full-length cDNA clones, although they lack a signal sequence. For PSEC242, a signal sequence could be found at the N-terminus, if the translation is initiated from the third ATG.

PSEC0242: No. 3 ATG, ATGpr1 0.82, SP-Yes, ORF 171-1343 391 aa, Signal peptide 24;

These results are shown below. The data are shown in the following order, subsequent to each clone name. Each data is discriminated by "//".

Clone name//
Size of cDNA//
Number of amino acid residues composing the predicted amino acid sequence//
Number of ATG counted from the N-terminus//
Maximal ATGpr1 value//
Presence or absence of signal sequences, or prediction of signal sequence by PSORT, prediction of membrane proteins by MEMSTAT and SOSUI//
Annotation:

PSEC0012//C-NT2RM1000853//1499//183//1//0.82//125/ 183 (68.3%) aa identity to fugu putative protein 2 (PUT2).

PSEC0129//C-PLACE1004170//1828//135//1//0.94//1564/ 1615 (96%) similarity to human chromosome 16q13/21 BAC clone CIT987SK-A-152E5 PSEC0220//C-HEMBA1005301//1584//365//1//0.94//354/365 (96%) aa id entity to mouse WNT-6 protein precursor; 1084/1310 (82%) similarity to mouse Wnt-6 mRNA PSEC0242//C-NT2RP3000266//3017//401//1//0.90//No & transmembrane//242/242 (100%) similarity to human Newcastle disease virus inducible protein mRNA, partial 31 UTR region; 85/341 (24%) aa identity to human myosin heavy chain.

PSEC0256//C-NT2RP3003549//3520//612//1//0.89//No & transmembrane//97/362 (26%) aa identity to rat cadherin-6 precursor; 1174/1394 (84%) similarity to mRNA for KIAA0345.

EXAMPLE 2

Expression of the Proteins Promoting or Preventing Amyloid β Protein Aggregation COS cells (6×10⁶ cells/dish) were seeded, and the expression plasmids (10 μg) obtained in Example 1 were added together with 10 μl of LIPOFECTAMINE (Gibco BRL) to transfect the COS7 cells. The recombinant cells thus created, which expressed the gene of interest were cultured in D-MEM medium (+10% FCS, Pc. Sm.) for three days. Supernatant of the cultured medium was collected as a supernatant fraction.

EXAMPLE 3

Amyloid-β Aggregation Reaction

The supernatants obtained in Example 2 were used to screen for proteins that promote or suppress amyloid-β protein aggregation. In principle, the experiments were conducted according to *Methods in Enzymology*, Volume 309 (1999) p 274–284. Instead of A 40 and A 42, which are commonly found in vivo, A 1–28 consisting of 28 amino acid residues from the N-terminus of A, which is considered to aggregate to a similar extent as A 40 and A 42, was used in the experiments. Experiments as shown below were conducted, and as a result, five clones showing augmented promotion or suppression of aggregation were selected from 108 clones. Experiment method and the activities of the five selected clones are shown below.

(Experiment Method)

Three microliters of 1 mM Aβ1–28 (Bachem) was added to 17 μl of the culture supernatant obtained in Example 2, and the reaction was initiated by adding 10 μl of 300 mM sodium acetate buffer (pH 5.2). After 24 hours, 200 μl of 10 μM thioflavin-T (in 50 mM potassium phosphate) was added to 5 μl of the reaction sample. Aβ aggregation was determined by measuring the fluorescence intensity (excitation 450 nm, emission 482 nm). Synthesized Aβ40-1 (a peptide having the inverse sequence of Aβ40) was added to the control to a concentration of 100 μM, instead of adding the culture supernatant. The results are shown in the table below. In the table, relative fluorescence intensities are shown, when the fluorescence intensity of the Aβ1–28 aggregation resulting from the addition of Aβ40-1 is taken to be 100%.
Table. 1 Changes of fluorescence intensity due to Aβ1–28 aggregates resulting from addition of Aβ40-1

| Protein | Fluorescence Intensity |
| --- | --- |
| PSEC0012 (supernatant containing product expressed from the clone of SEQ ID NO: 1) | 24% |
| PSEC0129 (supernatant containing the product expressed from the clone of SEQ ID NO: 3) | 24% |
| PSEC0220 (supernatant containing the product expressed from the clone of SEQ ID NO: 5) | 250% |
| PSEC0242 (supernatant containing the product expressed from the clone of SEQ ID NO: 7) | 16% |
| PSEC0256 (supernatant containing the product expressed from the clone of SEQ ID NO: 9) | 460% |

The proteins expressed from the clones comprising the polynucleotides of SEQ ID NOs: 1, 3 and 7 in the sequence list prevent aggregation of amyloid β protein, and the proteins expressed from the clones comprising the polynucleotides of SEQ ID NOs: 5 and 9 in the sequence list promote aggregation of amyloid β protein.

Furthermore, deposition of aggregated synthetic Aβ was confirmed through microscopic observation after staining with Congo red.

EXAMPLE 4

Gene Expression Analysis in Patients with Alzheimer's Disease

Expression levels of the gene were compared between healthy subjects and patients with Alzheimer's disease. The primers shown below were prepared for each clone, and quantitative PCR was conducted using hippocampal cDNA as template. Hippocampal cDNA from an Alzheimer's disease patient (age 60) (NO. 0550903) and one from a healthy subject (age 28) (NO. 0510069) were purchased from BioChain Institute Inc. and used. Analysis of the expression levels was performed using PE Applied Biosystems PRISM 7700 according to the protocol for quantitative PCR using SYBR Green (P/N 4304965). The four sets of primers used for PCR are as follows:

```
PSEC012-894F:
GTGGATGCGATCTGTCTCTCC      (SEQ ID NO. 15)

PSEC012-1049R:
TGCAGAAAGGAACACATGCTG      (SEQ ID NO. 16)

PSEC129-190F:
CTTCCATGCTTCAGCTGTGG       (SEQ ID NO. 17)

PSEC129-340R:
GCCCTGGTCTGTATACCTGGG      (SEQ ID NO. 18)

PSEC242-599F:
CTACGACCTGAGCCAGTGCA       (SEQ ID NO. 19)

PSEC242-749R:
GAGGGCTTGGAGCTGCTGT        (SEQ ID NO. 20)

PSEC256-1502F:
GCATTCTACGGGCTGGTCC        (SEQ ID NO. 21)

PSEC256-1652R:
GGGTTGCCTGGTCCGTATT        (SEQ ID NO. 22)
```

The expression level was reduced in the Alzheimer's disease patient, compared to the healthy subject, to 1/2 for PSEC012, 1/10 for PSEC129, and 1/9 for PSEC242. On the contrary, the expression level of PSEC256 was increased 1.5 folds in the Alzheimer's disease patient.

INDUSTRIAL APPLICABILITY

The present invention provides proteins that suppress or promote aggregation and deposition of amyloid-β protein, and polynucleotides encoding the proteins. The proteins of the present invention and the polynucleotides encoding the proteins are useful as pharmaceutical agents for treating and preventing diseases including Alzheimer's disease, and for diagnosing these diseases. Also, the present invention has enabled screening for a compound that suppresses or promotes aggregation of amyloid-β protein. It is hoped that the screening method of the present invention would be used for developing effective therapeutic agents for Alzheimer's disease that prevent amyloid-β aggregation.

The invention claimed is:

1. A polypeptide which (a) suppresses or promotes the aggregation of amyloid-β or (b) which is an immunogenic polypeptide, and which is encoded by an isolated polynucleotide selected from the group consisting of:
   (a) a polynucleotide that comprises a polynucleotide sequence as set forth in SEQ ID NO: 3, 5, 7 or 9,
   (b) a polynucleotide that encodes a polypeptide having an amino acid sequence as set forth in SEQ ID NO: 4, 6, 8 or 10,
   (c) a polynucleotide that hybridizes under stringent conditions to a polynucleotide comprising a polynucleotide sequence as set forth in SEQ ID NO: 3, 5, 7 or 9, wherein the stringent conditions comprise washing in 0.1×SSC and 0.1% SDS at 65° C.,
   (d) a polynucleotide that shows at least 95% homology to a polynucleotide sequence as set forth in SEQ ID NO: 3, 5, 7 or 9, and
   (e) a fragment of the polynucleotide of (a), (b), (c) or (d).

2. The polypeptide of claim 1, which suppresses the aggregation of amyloid-β protein.

3. The polypeptide of claim 1, which promotes the aggregation of amyloid-β protein.

4. The polypeptide of claim 1 which is immunogenic.

5. The polypeptide of claim 1 which is encoded by a polynucleotide sequence as set forth in SEQ ID NO: 3, 5, 7 or 9.

6. The polypeptide of claim 1 which comprises an amino acid sequence as set forth in SEQ ID NO: 4, 6, 8 or 10.

7. The polypeptide of claim 1 which is encoded by a polynucleotide that hybridizes under stringent conditions to a polynucleotide comprising a nucleotide sequence as set forth in SEQ ID NO: 3, 5, 7 or 9, wherein the stringent conditions comprise washing in 0.1×SSC and 0.1% SDS at 65° C.

8. The polypeptide of claim 1 which is encoded by a polynucleotide which shows at least 95% homology to a polynucleotide sequence as set forth in SEQ ID NO: 3, 5, 7 or 9.

9. The polypeptide of claim 1 which is encoded by a fragment of SEQ ID NO: 3, 5, 7 or 9.

10. A composition comprising the polypeptide of claim 1 and a pharmaceutically acceptable carrier or vehicle.

11. The composition of claim 10, wherein said polypeptide is encoded by a polynucleotide comprising SEQ ID NOS: 3 or 7 and inhibits amyloid-β-protein aggregation.

12. The composition of claim 10, wherein said polypeptide is encoded by a polynucleotide comprising SEQ ID NOS: 5 or 9 and which enhances amyloid-β-protein aggregation.

13. A method for inhibiting amyloid-β aggregation comprising contacting a sample containing amyloid-β with the polypeptide of claim 1.

14. A method for enhancing amyloid-β aggregation comprising contacting a sample containing amyloid-β with the polypeptide of claim 1.

15. A method for treating Alzheimer's Disease comprising administering to a subject in need thereof a polypeptide of claim 1 which inhibits amyloid-β aggregation.

16. A method for producing an antibody that binds to the polypeptide of claim 1, comprising immunizing an animal with the polypeptide of claim 1.

17. An immunological assay comprising:
   contacting the polypeptide of claim 1 with a sample containing an antibody, and
   monitoring the binding of antibody in said sample with the polypeptide of claim 1,
   wherein binding of antibodies in said sample to said polypeptide is indicative of the presence of antibodies that immunologically react with the polypeptide of claim 18 or inhibit its ability to suppress or promote the aggregation or deposition of amyloid β protein.

18. A method of screening for a compound that regulates the activity of the polypeptide of claim 1, wherein said method comprises:
   (a) contacting a candidate compound with said polypeptide, or with a cell expressing said polypeptide, in the presence of amyloid-β protein,
   (b) detecting the aggregation or deposition of amyloid-β protein, and
   (c) selecting a candidate compound that regulates the aggregation or deposition of amyloid-β protein.

* * * * *